US011098298B2

(12) United States Patent
Buchberger et al.

(10) Patent No.: US 11,098,298 B2
(45) Date of Patent: Aug. 24, 2021

(54) METHOD FOR RECOMBINANT PRODUCTION OF HORSESHOE CRAB FACTOR C PROTEIN IN PROTOZOA

(71) Applicant: BIOMÉRIEUX DEUTSCHLAND GMBH, Nürtingen (DE)

(72) Inventors: Bernd Buchberger, Zeitlarn/Laub (DE); Holger Grallert, Weilheim/Obb. (DE); Sonja Molinaro, Weilheim/Obb. (DE)

(73) Assignee: BIOMÉRIEUX DEUTSCHLAND GMBH, Nürtingen (DE)

( * ) Notice: Subject to any disclaimer, the term of this patent is extended or adjusted under 35 U.S.C. 154(b) by 0 days.

(21) Appl. No.: 16/400,520

(22) Filed: May 1, 2019

(65) Prior Publication Data

US 2019/0256836 A1  Aug. 22, 2019

Related U.S. Application Data

(62) Division of application No. 15/635,301, filed on Jun. 28, 2017, now Pat. No. 10,323,238, which is a division of application No. 14/649,765, filed as application No. PCT/EP2013/075517 on Dec. 4, 2013, now Pat. No. 9,725,706.

(60) Provisional application No. 61/734,002, filed on Dec. 6, 2012.

(30) Foreign Application Priority Data

Dec. 5, 2012 (EP) .................................... 12195742

(51) Int. Cl.
*C12N 9/64* (2006.01)
*G01N 33/579* (2006.01)

(52) U.S. Cl.
CPC ......... *C12N 9/6424* (2013.01); *C12N 9/6408* (2013.01); *C12Y 304/21084* (2013.01); *G01N 33/579* (2013.01); *C12N 2800/10* (2013.01); *C12N 2800/22* (2013.01)

(58) Field of Classification Search
None
See application file for complete search history.

(56) References Cited

U.S. PATENT DOCUMENTS

| 5,858,706 A | 1/1999 | Ding et al. |
| 6,645,724 B1 | 11/2003 | Ding et al. |
| 6,849,426 B2 | 2/2005 | Chen et al. |
| 2003/0054432 A1 | 3/2003 | Chen et al. |

FOREIGN PATENT DOCUMENTS

| JP | 2003-513632 | 4/2003 |
| WO | WO 1999/015676 | 4/1999 |
| WO | WO 2001/032896 | 5/2001 |
| WO | WO 2003/002976 | 1/2003 |
| WO | WO 2012/118226 | 9/2012 |

OTHER PUBLICATIONS

"Factor C Precursor [Tachypleus tridentatus]", GenBank Accession No. AAL75577, 2002.
Basile et al., "Recombinant protein expression in Leishmania tarentolae," *Molecular Biotechnology*, 43(3):273-278, 2009.
Beverly and Clayton, "Transfection of Leishmania and Trypanosoma brucei by electroporation," *Methods Mol. Biol.*, 21:333-348, 1993.
Breitling et al., "Non-pathogenic trypanosomatid protozoa as a platform for protein research and production," *Protein Expression and Purification*, 25:209-218, 2002.
Coburn et al., "Stable DNA transfection of a wide range of trypanosomatids," *Mol. Biochem. Parasitol.*, 46:169-179, 1991.
Ding et al., "Expression of full length and deletion homologues of Carcinoscorpius rotundicauda Factor C in *Saccharomyces cerevisiae*: immunoreactivity and endotoxin binding," *Journal of Endotoxin Research*, 4(1):33-43, 1997.
Ding et al., "Molecular cloning and sequence analysis of factor C cDNA from the Singapore horseshoe crab, *Carcinoscorpius rotundicauda*," *Molecular Marine Biology and Biotechnology*, 4:90-103, 1995.
Ding et al., "Two forms of factor C from the amoebocytes of Carcinoscorpius rotundicauda: purification and characterisation," *Biochimica et Biophysica Acta*, 1202:149-156, 1993.
Dortay and Mueller-Roeber, "A highly efficient pipeline for protein expression in Leishmania tarentolae using infrared fluorescence protein as marker," *Microbial Cell Factories*, 9(29), 10 pages, 2010.
Dwarakanath et al., "Expression of Carcinoscorpius rotundicauda factor C cDNA," *Biochem. Mol. Biol. Intl.*, 35:841-849, 1995.

(Continued)

*Primary Examiner* — Suzanne M Noakes
(74) *Attorney, Agent, or Firm* — Parker Highlander PLLC

(57) ABSTRACT

The present invention provides a novel method for the recombinant production of Factor C protein from horseshoe crab using a parasitic protozoan expressing the Factor C protein. In particular, the present invention provides a parasitic protozoan host cell harbouring a polynucleotide encoding horseshoe crab Factor C protein, and a method for producing Factor C protein comprising culturing said parasitic protozoan host cell under conditions such that the cells express the horseshoe crab Factor C protein. Furthermore, the present invention provides recombinant Factor C protein produced by the novel method and its use in the detection and/or removal of endotoxin.

10 Claims, 1 Drawing Sheet
Specification includes a Sequence Listing.

(56) References Cited

OTHER PUBLICATIONS

Dwarakanath et al., "Recombinant COS-1 cells express Carcinoscorpius rotundicauda Factor C," *Biotechnology Letters*, 19:357-361, 1997.
English translation of Office Communication issued in Korean Patent Application No. 10-2015-7017635, dated Nov. 14, 2017.
European Search Report issued in European Patent Application No. 12195742, dated Apr. 17, 2013.
Gazdag et al., "Purification and crystallization of human Cu/Zn superoxide dismutase recombinantly produced in the protozoan Leishmania tarentolae," *Acta. Cryst. F Structural Communications*, F66:871-877, 2010.
Heymayatkar et al., "Increased expression of recombinant human tissue plasminogen activator in Leishmania tarentolae," *Biotechnology Journal*, 5(11):1198-1206, 2010.
Muta et al., "Limulus factor C. An endotoxin-sensitive serine protease zymogen with a mosaic structure of complement-like, epidermal growth factor-like, and lectin-like domains," *J. Biol. Chem.*, 266:6554-6561, 1991.
Nakamura et al., "Lipopolysaccharide-sensitive serine-protease zymogen (factor C) found in Limulus hemocytes. Isolation and characterization," *Eur. J. Biochemi.*, 154:511-521, 1986.
NCBI Accession No. P28175.1, 1991.
Niimi, "Recombinant Protein Production in the Eukaryotic Protozoan parasite Leishmania tarentolae: A Review," In: *Methods in Molecular Biology: Recombinant Gene Expression, Reviews and Protocols*, Ed. A Lorence; Humana Press, vol. 824, Chapter 15, pp. 307-315, 2012.
Office Communication issued in Japanese Patent Application No. 2015-545998, dated Jul. 25, 2016. (English translation of Japanese text).
Office Communication issued in U.S. Appl. No. 14/649,765, dated Aug. 29, 2016.
Office Communication issued in U.S. Appl. No. 14/649,765, dated Jan. 22, 2016.
Office Communication issued in U.S. Appl. No. 14/649,765, dated Oct. 5, 2015.
Office Communication issued in U.S. Appl. No. 15/635,301, dated Aug. 22, 2017.
Office Communication issued in U.S. Appl. No. 15/635,301, dated Apr. 30, 2018.
PCT International Preliminary Report on Patentability issued in International Patent Application No. PCT/EP2013/075517, dated Mar. 4, 2015.
PCT International Search Report issued in International Patent Application No. PCT/EP2013/075517, dated Mar. 6, 2014.
Ross, "Intranuclear neuronal inclusions: a common pathogenic mechanism for glutamine-repeat neurodegenerative diseases?" *Biotechnology Letters*, 19:1147-1150, 1997.
Soleimani et al., "Expression of human tissue plasminogen activoator in the trypanosomatid protozoan Leishmania tarentolae," *Biotechnol. Appl. Biochem.*, 48:55-61, 2007.
Tokunaga et al., "Further studies on lipopolysaccharide-sensitive senile protease zymogen (factor C): its isolation from Limulus polyphemus hemocytes and identification as an intracellular zymogen activated by alpha-chymotrypsin, not by trypsin," *J. Biochem.*, 109(1):150-157, 1991.
Wang et al., "Functional expression of full length Limulus Factor C in stably transformed Sf9 cells," *Biotechnology Letters*, 23:71-76, 2001.
Wang et al., "Modular arrangement and secretion of a multidomain serine protease. Evidence for involvement of proline-rich region and N-glycans in the secretion pathway," *J. Biol. Chem.*, 277:36363-36372, 2002.

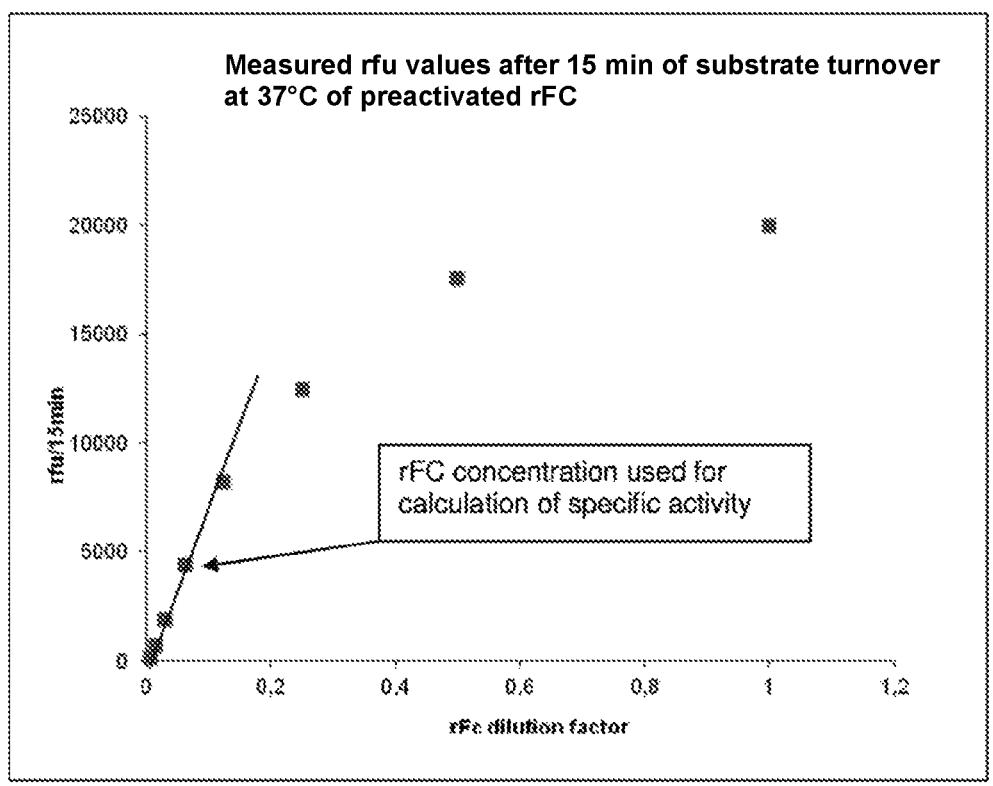

METHOD FOR RECOMBINANT PRODUCTION OF HORSESHOE CRAB FACTOR C PROTEIN IN PROTOZOA

This application is a divisional application of U.S. patent application Ser. No. 15/635,301, filed Jun. 28, 2017, which is a divisional application of U.S. patent application Ser. No. 14/649,765, filed Jun. 4, 2015, issued as U.S. Pat. No. 9,725,706, which is a national phase application under 35 U.S.C. § 371 of International Application No. PCT/EP2013/075517, filed Dec. 4, 2013, which claims the benefit of priority to U.S. Provisional Patent Application No. 61/734,002, filed Dec. 6, 2012 and to European Patent Application No. 12195742.7, filed Dec. 5, 2012. The entire contents of the above-referenced disclosures are specifically incorporated herein by reference.

BACKGROUND INFORMATION

The sequence listing that is contained in the file named "GRUNP0003USD2_ST25.txt", which is 26 KB (as measured in Microsoft Windows®) and was created on Apr. 1, 2019, is filed herewith by electronic submission and is incorporated by reference herein.

TECHNICAL FIELD OF THE INVENTION

The present invention provides a novel method for the recombinant production of Factor C protein from horseshoe crab using a parasitic protozoan expressing the Factor C protein. Accordingly, the present invention provides a parasitic protozoan host cell harbouring a polynucleotide encoding horseshoe crab Factor C protein and a method for producing Factor C comprising culturing said parasitic protozoan host cell under conditions such that the cells express the horseshoe crab Factor C protein. The present invention provides recombinant horseshoe crab Factor C protein produced by the novel method and its use in the detection and/or removal of endotoxin.

BACKGROUND ART

Endotoxin, also known as lipopolysaccharide (LPS), is an integral component of the Gram-negative bacterial cell membrane and is responsible for many, if not all, of the toxic effects that occur during Gram-negative bacterial sepsis.

LPS from Gram-negative bacteria induces the amoebocytes of horseshoe crabs to aggregate and to degranulate. Presumably, the LPS-induced coagulation cascade represents an important defense mechanism used by horseshoe crabs against invasion by Gram-negative bacteria. The amoebocyte lysate constituted as the *Limulus* amoebocyte lysate (LAL) test has been used for decades as a tool for detecting trace concentrations of endotoxin (LPS) in solution. The molecular mechanism of coagulation in horseshoe crab has been established and it involves a protease cascade. This cascade is based on 3 kinds of serine protease zymogens, Factor C, Factor B, proclotting enzyme, and one clottable protein, coagulogen. Being the initial activator of the clotting cascade, Factor C functions as a biosensor that responds to LPS. Once Factor C is "activated" by LPS, the active moiety created has the ability to activate Factor B and to hydrolyse synthetic tripeptide substrates.

Factor C activity is the basis of a very sensitive assay for femtogram levels of endotoxin used in the quality control of pharmaceutical products and the like. The importance of Factor C in the detection of endotoxin has thus led to the expression of recombinant Factor C (rFC) as an alternative source that should alleviate the recognized drawbacks with conventional amoebocyte lysate like seasonal variation in the sensitivity of detection of endotoxin.

For endotoxin specific assays, Factor C protein has been purified and cloned. Upon activation by LPS, recombinant Factor C acts on a synthetic substrate present in the assay mixture to generate a detectable signal, thereby indicating the presence of LPS in a given sample. In particular, a fluorogenic substrate produces a fluorescent signal in proportion of the endotoxin concentration in the sample. Factor C protein has been purified and cloned for its application in endotoxin-specific assays.

Nakamura et al. (1986, Eur. J. Biochem. 154:511-521) describe the isolation and characterization of native Factor C protein from the horseshoe crab *Tachypleus tridentatus*. The cDNA sequence encoding Factor C protein from *T. tridentatus* was published by Muta et al. (1991, J. Biol. Chem. 266:6554-6561). The cDNA sequence encoding Factor C protein from the horseshoe crab *Carcinoscorpius rotundicauda* was published by Ding et al. (1995, Molecular Marine Biology and Biotechnology 4:90-103).

The recombinant expression of Factor C from *C. rotundicauda* in *E. coli* was described in Roopashree et al. (1995, Biochem. Mol. Biol. Intl. 35:841-849). Here, the expression of a 108 kDa proenzyme and the activated forms of 78 kDa and 52 kDa was shown by immunodetection.

The recombinant expression of Factor C protein from *C. rotundicauda* in the yeast *Pichia pastoris* is described in Ding et al. (1996, U.S. Pat. No. 5,858,706). The recombinant expression of Factor C protein from *C. rotundicauda* in *Saccharomyces cerevisiae* is described in Dwarakanath et al. (1997, Biotechnology Letters 19:1147-1150).

The recombinant expression of Factor C protein from *C. rotundicauda* in mammalian COS-1 cells is described in Dwarakanath et al. (1997, Biotechnology Letters 19:357-361). Here, Factor C protein was expressed and protein bands with a molecular weight of 132 kDa, 130 kDa and 63 kDa were detected. The proteins were not secreted, not soluble, and not active, but were rather insoluble, associated with the cell debris fraction.

The recombinant expression of Factor C protein from *C. rotundicauda* in insect cells (stable transfected Sf9 cells) is described in Wang et al. (2001, Biotechnology Letters 23:71-76). Here, Factor C protein was secreted into the supernatant with a molecular weight of 132 kDa, which indicated glycosylation of the protein. The Factor C obtained was functionally active in the sense that it could bind endotoxin (LPS). However, no conversion into an enzymatically active protease was shown. The recombinant expression of Factor C protein from *C. rotundicauda* in insect cells is also described in Wang et al. (2002, J. Biol. Chem. 277:36363-736372). Here, Factor C was cloned and transfected into *Drosophila* S2 cells and was expressed as a glycosylated soluble protein, which was secreted into the culture supernatant. The recombinant Factor C protein was capable of binding LPS, but was not cleaved to become an enzymatically active protease. The recombinant expression of Factor C protein from *C. rotundicauda* in insect cells is furthermore described in U.S. Pat. No. 6,645,724 using the baculovirus system for expression in Sf9 cells.

Factor C protein is a complex eukaryotic protein, which requires several conversion steps and secondary modifications to become an active protease. The recombinant expression in prokaryotes (e.g., *E. coli*) does not provide glycosylation, cleavage into H-chain and L-chain and correct disulfide bond formation. The cytosolic expression in simple eukaryotic expression systems (e.g., yeast) provided Factor C, which was capable to bind LPS, but which was not activated upon LPS binding, i.e., there was no conversion from the zymogen form into an active protease. When using yeast cells (*Pichia* or *Saccharomyces*) for expression, it was not possible to obtain recombinant Factor C as secreted protein. The expression in a mammalian cell line did also not provide active secreted protein. Furthermore, the expression in stable transformed insect cells provided secreted protein, which was capable to bind LPS. However, the activation by LPS was not shown in this system. Finally, the expression in insect cells using a baculovirus expression system provided secreted Factor C protein, which was capable to bind LPS, and which was converted into an active serine protease zymogen upon LPS binding.

From all experience so far gained it was concluded by the experts succeeding with the expression of active Factor C protein in insect cells, that "expression in insect cells rather than in a prokaryotic or simple eukaryotic expression system is suitable for producing rFC with full biological activity. Furthermore, horseshoe crabs and insects belong to the same phylum, Arthropoda, and so insect cells might more closely resemble the cells of the horseshoe crab than yeast cells in their physiology and biochemistry. Thus, rFC produced in insect cells might more closely resemble the protein as purified from the horseshoe crab and retain the bioactivity of having a serine protease activity activated by LPS" (see WO 99/15676 on page 2, "Summary of the Invention").

Since that time, i.e., more than 13 years after the publication of WO 99/15676, no further attempts have been made with respect to the recombinant production of active Factor C protein. Obviously, in view of the results obtained over the years from recombinant expression in various host systems, and in view of the unequivocal assessment given by the top experts in the field in WO 99/15676, the baculovirus expression system in insect host cells was considered as the gold standard for recombinant production of active Factor C protein.

SUMMARY OF THE INVENTION

The present invention provides a novel method for the recombinant production of Factor C protein from horseshoe crab using a parasitic protozoan expressing the Factor C protein. In particular, the present invention provides a parasitic protozoan host cell harbouring a polynucleotide encoding horseshoe crab Factor C protein, and a method for producing Factor C protein comprising culturing said parasitic protozoan host cell under conditions such that the cells express the horseshoe crab Factor C protein. Furthermore, the present invention provides recombinant Factor C protein produced by the novel method and its use in the detection and/or removal of endotoxin.

In particular, aspects of the present invention are:
[1] A parasitic protozoan, which is characterized by harbouring a polynucleotide encoding Factor C protein.
[2] The parasitic protozoan of [1], wherein said polynucleotide is comprised by a nucleic acid molecule, preferably a vector, introduced into the parasitic protozoan host cell.
[3] The parasitic protozoan of [1] or [2], wherein the parasitic protozoan is a member of the order Trypanosomatida.
[4] The parasitic protozoan of any one of [1] to [3], wherein the parasitic protozoan is a member of the genus *Leishmania*.
[5] The parasitic protozoan of any one of [1] to [4], wherein the parasitic protozoan is *Leishmania tarentolae*.

[6] The parasitic protozoan of any one of [1] to [5], wherein said polynucleotide encodes Factor C protein from *Limulus polyphemus*, *Carcinoscorpius rotundicauda*, *Tachypleus tridentatus*, or *Tachypleus gigas*.
[7] The parasitic protozoan of any one of [1] to [6], wherein said polynucleotide encodes Factor C protein having the amino acid sequence of SEQ ID NO: 4.
[8] A method for producing Factor C protein comprising the steps of: (a) culturing a parasitic protozoan of any one of [1] to [7] under conditions such that the cells express the Factor C protein encoded by the polynucleotide; and (b) recovering the Factor C protein produced in step (a) from the cell culture.
[9] The method of [7] or [8], wherein said Factor C protein is accumulated in the cell culture medium.
[10] The method of [8] or [9], wherein the Factor C protein produced exhibits serine protease activity upon binding to endotoxin.
[11] Factor C protein obtainable by the method of [8]. [12]. Use of Factor C protein produced by the method of any one of [8] to [10] in a method for endotoxin detection or in a method for endotoxin removal.
[13] Use of Factor C protein of [11] in a method for endotoxin detection or in a method for endotoxin removal.
[14] An assay or kit for endotoxin detection or endotoxin removal, comprising Factor C protein produced by the method of any one of [8] to [10], or Factor C protein of [11].
[15] A process of generating a parasitic protozoan host cell that produces Factor C protein, comprising the steps of: (a) introducing a nucleic acid molecule, preferably a vector, comprising a polynucleotide encoding Factor C protein into a parasitic protozoan, preferably a parasitic protozoan of the order Trypanosomatida, more preferably a member of the genus *Leishmania*, most preferably *Leishmania tarentolae*; and (b) selecting for one or more host cells produced in step (a) that express said Factor C protein.
[16] A parasitic protozoan host cell obtainable by the process of [15], comprising a polynucleotide encoding Factor C protein, wherein said polynucleotide is comprised by a nucleic acid molecule, preferably a vector, introduced into the parasitic protozoan host cell.

BRIEF DESCRIPTION OF THE DRAWINGS

FIG. 1: shows the plot of measured rfu values of LPS-activated recombinant Factor C (rFC) samples after 15 minutes substrate turnover at 37° C. in dependence of the rFC concentration. The rFC concentration used for calculation of the specific activity is indicated.

DETAILED DESCRIPTION OF THE INVENTION

Factor C from horseshoe crabs is well established for use in the detection and removal of endotoxin. Attempts have been made in the past to produce Factor C by recombinant expression as an alternative source to conventional amoebocyte lysate, the aqueous extract of blood cells (amoebocytes) from horseshoe crabs. Many attempts in the art on recombinant expression of Factor C failed because the recombinant Factor C (rFC) produced in various host cells has shown not to exhibit the biologic activity required for use in endotoxin detection methods. The host cells applied in the art were prokaryotic cells, simple eukaryotic cells and higher eukaryotic cells, and after years of intensive research it was concluded by the experts in the field that expression in insect cells rather than in a prokaryotic or simple eukaryotic expression system is suitable for producing rFC with full biological activity. In connection with this, it was explained by the experts in the field that horseshoe crabs and insects belong to the same phylum, Arthropoda, and so insect cells might more closely resemble the cells of the horseshoe crab than yeast cells in their physiology and biochemistry. Thus, rFC produced in insect cells might more closely resemble the protein as purified from the horseshoe crab and retain the bioactivity of having a serine protease activity activated by LPS.

The present invention provides a novel method for the recombinant production of Factor C protein from horseshoe crab using a parasitic protozoan expressing the Factor C protein. In particular, the present invention provides a parasitic protozoan host cell harbouring a polynucleotide encoding heterologous Factor C protein from a horseshoe crab, and a method for producing recombinant Factohorseshoe cradr C protein from a horseshoe crab comprising culturing said parasitic protozoan host cell under conditions such that the cells express the recombinant Factor C protein. Furthermore, the present invention provides recombinant Factor C protein produced by the novel method and its use in the detection and/or removal of endotoxin.

Protozoans are simple unicellular eukaryotic organisms. The subject matter of the present invention was not obvious for the skilled person because the art has led away from using simple eukaryotic expression systems for successfully producing active Factor C protein, as explained herein above. Furthermore, it was surprising that the basic chaperone system of protozoans provide for a correct folding of recombinant Factor C, bearing in mind that more than 20 disulfide bonds have to be connected properly in order to obtain the Factor C protein. One could not expect that protozoan host cells of the present invention provide recombinant horseshoe crab Factor C, which allows the correct cleavage of the pre-pro-enzyme and the pro-enzyme into the active protease composed of a heavy (H) and a light (L) chain. In addition, the use of protozoa provided by the present invention for the expression of recombinant horseshoe crab Factor C protein has the following advantages:

First, while the use of insect cells for the recombinant production of Factor C protein is associated with high costs due to the fact that expensive special culture media are required, the use of protozoa is cheap because the required media are cheap, with equipment and culture conditions being similar to fermentation of bacteria. In addition, cultures of protozoans are relatively fast growing (rapid generation time) and easy to scale-up. Furthermore, once cloned, the recombinant expression host is stable and does not require the continuous preparation of infective virus stocks. The recombinant Factor C protein produced in protozoa cultures of the present invention has been shown to be secreted in good yield and in soluble form, and can easily be purified from the culture supernatant. Specifically, only one active form of Factor C is purified from the supernatant without degradation products. It is of note that the expressed recombinant protein is stable and no additives are required to protect the zymogen form.

Host Cells

The present invention provides a parasitic protozoan, which is characterized by harbouring a polynucleotide encoding heterologous Factor C protein. The parasitic protozoan provided by the present invention is used for the recombinant production of Factor C from a horseshoe crab. Therefore, the present invention provides a parasitic protozoan host cell for the recombinant production of horseshoe crab Factor C, wherein the parasitic protozoan host cell is characterized by harbouring a polynucleotide encoding heterologous Factor C protein.

The host cell of the present invention for the recombinant production of horseshoe crab Factor C is a parasitic protozoan host cell. Preferably, the parasitic protozoan host cell is a kinetoplastid parasitic protozoan host cell. The common taxonomic feature of these host cells is a single mitochondrion with a dense mass of extranuclear DNA. The region of the mitochondrion containing the DNA is termed the "kinetoplast", and the DNA is termed "kinetoplast DNA". Small subunit rRNA- and conserved protein-based phylogenies support the division of kinetoplastids into five orders: Prokinetoplastida, Neobodonida, Parabodonida, Eubodonida, and Trypanosomatida. Therefore, preferred kinetoplastid parasitic protozoa of the present invention are parasitic Prokinetoplastida, Neobodonida, Parabodonida, Eubodonida, or Trypanosomatida. Preferably, kinetoplastid parasitic protozoa of the present invention are parasitic trypanosomatids (i.e., parasitic Trypanosomatida). Since all members of the trypanosomatids are parasitic, simply the term "trypanosomatids" is used herein to describe parasitic trypanosomatids (i.e., parasitic Trypanosomatida).

The trypanosomatids consist of the monogenetic genera such as *Crithidia*, *Leptomonas*, and *Blastocrithidia*, and the digenetic genera such as *Leishmania* and *Trypanosoma*. In the present invention, preferred kinetoplastid parasitic protozoa are digenetic trypanosomatids (i.e., digenetic members of the order Trypanosomatida). More preferably, the host cell of the present invention is a member of the genus *Leishmania*. Still more preferably, the host cell of the present invention is *Leishmania major* or *Leishmania tarentolae*. In the present invention, the most preferred host cell is *Leishmania tarentolae*.

In various embodiments, the host cell of the present invention is a member of the genus *Trypanosoma*. In preferred embodiments, the host cell of the present invention is selected from the species *Trypanosoma brucei* and *Trypanosoma theileri*.

Although trypanosomes are important causes of human and animal disease, many species are non-pathogenic. The trypanosomatid protozoa of the present invention are preferably non-pathogenic kinetoplastid parasitic protozoa (non-pathogenic Kinetoplastidae), more preferably non-pathogenic trypanosomatid protozoa (non-pathogenic Trypanosomatidae), still more preferably non-pathogenic *Leishmania*. Preferred non-pathogenic species of Kinetoplastidae include, but are not limited to, *Leishmania tarentolae*, *Crithidia fasciculata*, *Wallaceina inconstans* (former *Proteomonas inconstans*), *Leptomonas collos*, *Leptomonas* sp. and *Leptomonas seymouri*. The most preferred non-pathogenic protozoan of the present invention is *Leishmania tarentolae*.

In various embodiments, the parasitic protozoan host cells of the present invention are attenuated pathogenic protozoan host cells, i.e., their pathogenicity has been attenuated, preferably genetically attenuated. One approach to attenuate pathogens is targeted gene deletion. Therefore, genetically attenuated trypanosomatid parasites (i.e., trypanosomatid parasitic protozoa) can be obtained by deletion of selected genes (e.g., genes encoding virulence factors). Gene deletion takes advantage of the fact that this parasite can undergo homologous recombination between endogenous and foreign DNA sequences artificially introduced in the cells. Attenuated parasitic protozoans, preferably attenuated trypanosomatid parasites, used in the present invention have an attenuated virulence, in particular an attenuated virulence for humans.

It will be understood that throughout the specification and the claims the use of terms like "non pathogenic Kinetoplastidae" or "non-pathogenic Trypanosomatidae" refers not only to organisms/hosts encompassed in the aforementioned species, but also includes those species in alternate classification schemes, but which possess the same morphological and cultural characteristics or features defined above, and may be synonyms of "non pathogenic Kinetoplastidae" and "non-pathogenic Trypanosomatidae".

As used herein, the term non-pathogenic includes, but is not limited to, the meaning non-pathogenic to humans. In various embodiments, "non pathogenic" is defined by classification of the organisms in questions to the Biosafety Level 1.

In various embodiments, the protozoan host cell comprises a selectable marker, preferably a selectable marker gene.

Expression System

The present invention provides a protozoan host cell comprising a polynucleotide encoding a heterologous Factor C protein from a horseshoe crab. As used herein, heterologous protein means a protein which is not native to the host cell. The protozoan host cell of the present invention represents an expression system for the recombinant production of horseshoe crab Factor C protein. Therefore, the present invention provides an expression system comprising a parasitic protozoan host cell and a polynucleotide encoding a heterologous Factor C protein from a horseshoe crab, as well the use of the expression system for the expression of a heterologous Factor C protein from a horseshoe crab. While in various embodiments, the expression system provided by the present invention may comprise the host cell and the polynucleotide as separate means, it is preferred that the expression system provided by the present invention comprises a parasitic protozoan host cell, which already harbours the polynucleotide encoding the heterologous horseshoe crab Factor C protein.

In various embodiments, the polynucleotide coding for the heterologous horseshoe crab Factor C protein is operably linked to a suitable promoter sequence and, if appropriate, to post-transcriptional signal sequences, which are capable of directing expression of the polynucleotide encoding the Factor C protein in the host cell of the present invention. Preferably, the promoter is a promoter of an actively transcribed gene of a kinetoplastid parasitic protozoan. More preferably, the promoter is a promoter of an actively transcribed gene of a member of the order Trypanosomatida, still more preferably the promoter is a promoter of an actively transcribed gene of a member of the genus *Leishmania*, most preferably the promoter is a promoter of an actively transcribed gene of *Leishmania tarentolae.*

In various embodiments, the promoter is a strongly transcription initiating heterologous promoter.

The polynucleotide encoding horseshoe crab Factor C protein used in the present invention is a heterologous polynucleotide, in particular a heterologous polynucleotide encoding heterologous horseshoe crab Factor C protein. As used herein, heterologous polynucleotide means a polynucleotide which is not native to the host cell. In various embodiments, the transcription of the heterologous polynucleotide used in the present invention is controlled by a repressor-responsive element in connection with an incorporated and expressed repressor gene.

In various embodiments, at least one copy of the heterologous polynucleotide is located in an actively transcribed gene cluster of the protozoan host cell of the present invention. Preferably, the actively transcribed gene cluster is an rRNA gene cluster.

In various embodiments, the polynucleotide encoding the heterologous Factor C protein is flanked by 5' and 3' UTRs (untranslated or non-translated regions) of an actively transcribed gene of a kinetoplastid parasitic protozoan. Preferably, the polynucleotide encoding the heterologous Factor C protein is flanked by 5' and 3' UTRs of an actively transcribed gene of a member of the order Trypanosomatida, more preferably by 5' and 3' UTRs of an actively transcribed gene of a member of the genus *Leishmania*, and still more preferably by 5' and 3' UTRs of an actively transcribed gene of *Leishmania tarentolae.*

In various embodiments the polynucleotide encoding the heterologous Factor C protein is flanked by one or more signal sequences, which provide for, e.g., efficient secretion, splicing and/or polyadenylation of an actively transcribed gene of a kinetoplastid parasitic protozoan, i.e., the signal sequence is a signal sequence of an actively transcribed gene of a kinetoplastid parasitic protozoan. Preferably, the heterologous Factor C protein is flanked by one or more signal sequences of an actively transcribed gene of a member of the order Trypanosomatida, more preferably by one or more signal sequences of an actively transcribed gene of a member of the genus *Leishmania*, and still more preferably by one or more signal sequences of an actively transcribed gene of *Leishmania tarentolae.*

In various embodiments, the heterologous Factor C protein is flanked by the signal sequence derived from acid phosphatase of *Leishmania mexicana* (Wiese et al. 1995, EMBO J. 14:1067-1074).

In various embodiments, the expression system of the present invention is substantially free of the production of proteases, toxins and large amounts of other endogenously synthesized and secreted proteins of the host cell.

Factor C Nucleic Acid and Amino Acid Sequences and Variants Thereof

The Factor C protein encoded by a polynucleotide used in the present invention is a heterologous Factor C protein. The polynucleotide used in the present invention comprises a nucleic acid sequence encoding Factor C, which exhibits enzymatic activity like Factor C from a horseshoe crab. The scope of the present invention encompasses the use of polynucleotides encoding Factor C with an amino acid sequence as found in its natural source, i.e., an amino acid sequence of Factor C as obtainable from horseshoe crabs, as well as the use of polynucleotides encoding variants of a Factor C amino acid sequence as described herein. The scope of the present invention also encompasses the use of polynucleotides comprising a Factor C nucleic acid sequence as found in its natural source, i.e., a Factor C nucleic acid sequence as obtainable from horseshoe crabs, as well as the use of polynucleotides comprising a variant Factor C nucleic acid sequence as described herein. In any event, a polynucleotide used in the present invention encodes a Factor C protein, which shows Factor C-like enzymatic activity upon activation with endotoxin. The definition of "Factor C-like enzymatic activity" is given elsewhere herein.

In various embodiments, the polynucleotide used in the present invention encoding Factor C protein is modified by the insertion, deletion, addition, and/or substitution of one or more nucleic acids, with the proviso that the Factor C protein obtained from expression of such a modified polynucleotide in a parasitic protozoan host cell according to the present invention shows Factor C-like enzymatic activity upon activation with endotoxin, chymotrypsin (in particular α-chymotrypsin) or lipid A.

In various embodiments, the polynucleotide used in the present invention is the polynucleotide encoding the Factor C from *Tachypleus tridentatus* or *Tachypleus gigas*.

In various embodiments, the polynucleotide encodes the Factor C from *Carcinoscorpius rotundicauda*. In various embodiments, the polynucleotide encodes the Factor C from *Limulus polyphemus*. In various embodiments, the polynucleotide used in the present invention comprises the nucleic acid sequence shown in SEQ ID NO: 1 or SEQ ID NO: 3 of the sequence listing.

In various embodiments, the polynucleotide used in the present invention is at least 75% identical to a polynucleotide encoding the polypeptide having the amino acid sequence of SEQ ID NO: 4, and encodes a polypeptide exhibiting Factor C-like enzymatic activity. Preferably, the polynucleotide exhibits an identity of at least 85% or at least 95% identity to a polynucleotide encoding the polypeptide having the amino acid sequence of SEQ ID NO: 4, and encodes a polypeptide exhibiting Factor C-like enzymatic activity. More preferably, the polynucleotide exhibits an identity of at least 96% or at least 97% identity to a polynucleotide encoding the polypeptide having the amino acid sequence of SEQ ID NO: 4, and encodes a polypeptide exhibiting Factor C-like enzymatic activity. Even more preferably, the polynucleotide exhibits an identity of at least 98% or at least 99% identity to a polynucleotide encoding the polypeptide having the amino acid sequence of SEQ ID NO: 4, and encodes a polypeptide exhibiting Factor C-like enzymatic activity.

In various embodiments, the polynucleotide used in the present invention encodes a polypeptide, which has an amino acid sequence that is at least 75% identical to the amino acid sequence of SEQ ID NO: 4, and which exhibits Factor C-like enzymatic activity. Preferably, the polynucleotide encodes a polypeptide, which has an amino acid sequence that is at least 85% or at least 95% identical to the amino acid sequence of SEQ ID NO: 4, and which exhibits Factor C-like enzymatic activity. More preferably, the polynucleotide encodes a polypeptide, which has an amino acid sequence that is at least 96% or at least 97% identical to the amino acid sequence of SEQ ID NO: 4, and which exhibits Factor C-like enzymatic activity. Even more preferably, the polynucleotide encodes a polypeptide, which has an amino acid sequence that is at least 98% or at least 99% identical to the amino acid sequence of SEQ ID NO: 4, and which exhibits Factor C-like enzymatic activity.

In various embodiments, the polynucleotide used in the present invention is a polynucleotide, which hybridizes under stringent conditions to any of the polynucleotides described herein, wherein the hybridizing polynucleotide encodes a polypeptide, which exhibits Factor C-like enzymatic activity.

In various embodiments, the polynucleotide used in the present invention is at least 75% identical to the nucleotide sequence of SEQ ID NO: 1 or SEQ ID NO: 3, and encodes a polypeptide exhibiting Factor C-like enzymatic activity. Preferably, the polynucleotide used in the present invention is at least 85% or at least 95% identical to the nucleotide sequence of SEQ ID NO: 1 or SEQ ID NO: 3, and encodes a polypeptide exhibiting Factor C-like enzymatic activity. More preferably, the polynucleotide used in the present invention is at least 96% or at least 97% identical to the nucleotide sequence of SEQ ID NO: 1 or SEQ ID NO: 3, and encodes a polypeptide exhibiting Factor C-like enzymatic activity. Even more preferably, the polynucleotide used in the present invention is at least 98% or at least 99% identical to the nucleotide sequence of SEQ ID NO: 1 or SEQ ID NO: 3, and encodes a polypeptide exhibiting Factor C-like enzymatic activity.

In various embodiments, the polynucleotide used in the present invention comprises a part of the nucleotide sequence of the polynucleotide that is at least 75% identical to the nucleotide sequence of SEQ ID NO: 1 or SEQ ID NO: 3, and that encodes a polypeptide exhibiting Factor C-like enzymatic activity, wherein said part encodes a fragment, analog or functional derivative of the polypeptide having the amino acid sequence of SEQ ID NO: 2 or SEQ ID NO: 4, and wherein said fragment, analog or functional derivative exhibits Factor C-like enzymatic activity. Preferably, the polynucleotide comprises a part of the nucleotide sequence of the polynucleotide that is at least 85% or at least 95% identical to the nucleotide sequence of SEQ ID NO: 1 or SEQ ID NO: 3, and that encodes a polypeptide exhibiting Factor C-like enzymatic activity, wherein said part encodes a fragment, analog or functional derivative of the polypeptide having the amino acid sequence of SEQ ID NO: 2 or SEQ ID NO: 4, and wherein said fragment, analog or functional derivative exhibits Factor C-like enzymatic activity. More preferably, the polynucleotide comprises a part of the nucleotide sequence of the polynucleotide that is at least 96% or at least 97% identical to the nucleotide sequence of SEQ ID NO: 1 or SEQ ID NO: 3, and that encodes a polypeptide exhibiting Factor C-like enzymatic activity, wherein said part encodes a fragment, analog or functional derivative of the polypeptide having the amino acid sequence of SEQ ID NO: 2 or SEQ ID NO: 4, and wherein said fragment, analog or functional derivative exhibits Factor C-like enzymatic activity. Even more preferably, the polynucleotide comprises a part of the nucleotide sequence of the polynucleotide that is at least 98% or at least 99% identical to the nucleotide sequence of SEQ ID NO: 1 or SEQ ID NO: 3, and that encodes a polypeptide exhibiting Factor C-like enzymatic activity, wherein said part encodes a fragment, analog or functional derivative of the polypeptide having the amino acid sequence of SEQ ID NO: 2 or SEQ ID NO: 4, and wherein said fragment, analog or functional derivative exhibits Factor C-like enzymatic activity.

In various embodiments, the polynucleotide used in the present invention is the complement of the full length of any of the polynucleotides, which are described herein and which can be used in the present invention, wherein the complement polynucleotide encodes a polypeptide exhibiting Factor C-like enzymatic activity.

The present invention specifically encompasses the use of the nucleic acid sequences encoding Factor C from the horseshoe crab *Carcinoscorpius rotundicauda* as described in WO 99/15676. In particular, the present invention includes by reference the use of the representative nucleotide sequences presented as SEQ ID NO: 1 and SEQ ID NO: 3 of WO 99/15676. Likewise, the use of the amino acid sequences of SEQ ID NOs: 2 and 4 of WO 99/15676, which represent the amino acid sequences encoded by the nucleotide sequences of SEQ ID NO: 1 and SEQ ID NO: 3 of WO 99/15676, respectively, are explicitly included in the present invention by reference.

The sequences of SEQ ID NOs: 1 to 4 of WO 99/15676 do not correspond to SEQ ID NOs: 1 to 4 of the sequence listing of the present specification. Whenever reference is made in the present invention to any of the sequences of SEQ ID NOs: 1 to 4, any of the sequences of SEQ ID NOs: 1 to 4 of the sequence listing of the present specification is meant. In contrast, the sequences of SEQ ID NOs: 1 to 4 of WO 99/15676 are addressed herein by explicit reference to WO 99/15676, as shown in the preceding paragraph.

The scope of the present invention encompasses the recombinant production of a Factor C polypeptide encoded by any of the polynucleotides and nucleic acid molecules described herein. Of course, the scope of the present invention also encompasses the recombinant Factor C polypeptide obtained from any such production process.

In various embodiments, the amino acid sequence of the Factor C protein of the present invention is modified by the insertion, deletion, addition, and/or substitution of one or more amino acid residues, with the proviso that the Factor C protein having such a modified amino acid sequence after recombinant expression in a parasitic protozoan host according to the present invention shows Factor C-like enzymatic activity upon activation with endotoxin, chymotrypsin or lipid A.

The meaning of the term "one or more amino acid residues" in the preceding sentence varies depending on the positions of the amino acid residues in the three-dimensional structure of the Factor C protein and the types of the amino acid residues. More particularly, the said term means preferably 1 to 20 amino acid residues, more preferably 1 to 10 amino acid residues, still more preferably 1 to 5 amino acid residues, and even more preferably 1 to 3 amino acid residues. In various embodiments, the above-described insertion, deletion, addition, and/or substitution of one or more amino acids is a conservative mutation that maintains the enzymatic activity of the Factor C protein upon activation of the zymogen form by endotoxin, chymotrypsin or lipid A. An exemplary conservative mutation is a conservative substitution. The conservative substitution is, e.g., a mutation wherein substitution takes place mutually among Phe, Trp, and Tyr, if the substitution site is an aromatic amino acid; among Leu, Ile, and Val, if the substitution site is a hydrophobic amino acid; between Gln and Asn, if the substitution site is a polar amino acid; among Lys, Arg, and His, if the substitution site is a basic amino acid; between Asp and Glu, if the substitution site is an acidic amino acid; and between Ser and Thr, if the substitution site is an amino acid having a hydroxyl group. Examples of substitutions considered as conservative substitutions include in particular the substitution of Ser or Thr for Ala, the substitution of Gln, His, or Lys for Arg, the substitution of Glu, Gln, Lys, His, or Asp for Asn, the substitution of Asn, Glu, or Gln for Asp, the substitution of Ser or Ala for Cys, the substitution of Asn, Glu, Lys, His, Asp, or Arg for Gln, the substitution of Gly, Asn, Gln, Lys, or Asp for Glu, the substitution of Pro for Gly, the substitution of Asn, Lys, Gln, Arg, or Tyr for His, the substitution of Leu, Met, Val, or Phe for Ile, the substitution of Ile, Met, Val, or Phe for Leu, the substitution of Asn, Glu, Gln, His, or Arg for Lys, the substitution of Ile, Leu, Val, or Phe for Met, the substitution of Trp, Tyr, Met, Ile, or Leu for Phe, the substitution of Thr or Ala for Ser, the substitution of Ser or Ala for Thr, the substitution of Phe or Tyr for Trp, the substitution of His, Phe, or Trp for Tyr, and the substitution of Met, Ile, or Leu for Val.

The present invention encompasses any of the above-described insertion, deletion, addition, and/or substitution to the amino acid sequences of SEQ ID NO: 2 or 4.

The above-described insertion, deletion, addition, and/or substitution also encompasses a naturally occurring mutation due to difference in the individual strain or species among the horseshoe crabs from which the Factor C gene is derived. Furthermore, the above-described insertion, deletion, addition, and/or substitution also encompasses a mutation naturally occurring in the course of recombinant expression of the Factor C protein in the individual host cell.

In various embodiments, the Factor C protein produced by a method of the present invention has the amino acid sequence of Factor C from *Tachypleus tridentatus* or *Tachypleus gigas*. In various embodiments, the Factor C protein produced by a method of the present invention has the amino acid sequence of Factor C from *Carcinoscorpius rotundicauda*. In various embodiments, the Factor C protein produced by a method of the present invention has the amino acid sequence of Factor C from *Limulus polyphemus*. In various embodiments, the Factor C protein produced by a method of the present invention has the amino acid sequence of SEQ ID NO: 4.

In various embodiments, the polynucleotide used in the present invention encodes a polypeptide having the amino acid sequence of SEQ ID NO: 4, or a fragment, analog or functional derivative thereof, wherein said fragment, analog or functional derivative exhibits Factor C-like enzymatic activity. The present invention encompasses fragments, analogs and/or functional derivatives of any of the Factor C polypeptides described herein, as long as such fragments, analogs and/or functional derivatives show Factor C-like enzymatic activity upon activation with endotoxin, chymotrypsin or lipid A.

For the recombinant production of horseshoe crab Factor C according to the present invention, the parasitic protozoan comprises a polynucleotide encoding recombinant Factor C protein from a horseshoe crab. Therefore, the polynucleotide encoding Factor C protein from a horseshoe crab used in the present invention is a heterologous polynucleotide, more specifically a heterologous polynucleotide encoding a heterologous Factor C protein from a horseshoe crab.

For the sake of clarity, any variant of a horseshoe crab Factor C protein described herein is still considered to be a horseshoe crab Factor C protein, not at least in view of the fact that any variant described herein is defined to exhibit horseshoe crab Factor C-like enzymatic activity.

Factor C-Like Enzymatic Activity

Zymogens (or proenzymes) are precursors of enzymes. While zymogens are sometimes called inactive precursors of enzymes, the zymogen is not "inactive" in the sense that it has lost its activity (due to different factors), but rather is a molecule that needs to be activated in order to become an active enzyme.

Factor C from horseshoe crabs remains a zymogen until it encounters trace levels of endotoxin. Upon activation by endotoxin (or chymotrypsin or lipid A), horseshoe crab Factor C unequivocally exhibits full enzymatic activity, indicating the presence of endotoxin (e.g., in a sample to be assayed for endotoxin) by hydrolyzing a synthetic Factor C substrate, which forms a measurable/detectable product. The recombinant Factor C (rFC) of the present invention is produced as a zymogen like Factor C from its natural source. Furthermore, rFC of the present invention also remains a zymogen until it encounters trace levels of endotoxin. Upon activation by endotoxin (or chymotrypsin or lipid A), rFC of the present invention unequivocally exhibits full enzymatic activity like horseshoe crab Factor C from its natural source.

In view of the above, and just for the sake of clarity, it is noted that "Factor C-like enzymatic activity" means enzymatic activity of Factor C from a horseshoe crab as measured for the activated form. In other words, "Factor C-like enzymatic activity" means enzymatic activity of horseshoe crab Factor C activated by endotoxin, chymotrypsin or lipid A. Therefore, if recombinant Factor C protein produced by a method of the present invention is described herein to have or exhibit Factor C-like enzymatic activity, it is clear that the enzymatic activity of the activated zymogen is meant. In other words, "enzymatic activity of Factor C from a horseshoe crab" as used herein means "enzymatic activity of activated Factor C from a horseshoe crab" or "enzymatic activity of activated Factor C zymogen from a horseshoe crab".

In various embodiments, the terms "(recombinant) Factor C of the present invention" and "zymogen (recombinant) Factor C of the present invention" may be used interchangeably.

While the rFC directly obtained from a method of the present invention is a precursor of the Factor C enzyme, the zymogen rFC of the present invention is not "inactive" in the sense that it has lost its activity (due to different factors). Rather the zymogen rFC of the present invention is a molecule that needs to be activated in order to become an active enzyme.

The enzymatic activity of Factor C from a horseshoe crab specifically is hydrolytic activity, more specifically proteolytic activity, and still more specifically serine protease activity. Therefore, Factor C-like enzymatic activity as described herein specifically means horseshoe crab Factor C-like hydrolytic activity, more specifically horseshoe crab Factor C-like proteolytic activity, and still more specifically horseshoe crab Factor C-like serine protease activity.

The enzymatic activity of a horseshoe crab Factor C protein can be measured by, e.g., a chromogenic or fluorometric assay. In particular, the enzymatic activity of a horseshoe crab Factor C can be verified by, e.g., a detectable chromogenic or fluorogenic signal, which is produced due to cleavage/hydrolysis of a Factor C substrate by activated Factor C. Suitable assays for detecting Factor C activity are described in the art, and the one of ordinary skill will not have any problems in performing an assay for detecting/measuring the enzymatic activity of a given Factor C protein. Substrates for Factor C are also described and available in the art. The scope of the present invention encompasses the use of chromogenic and fluorogenic Factor C substrates, which include, but are not limited to, chromogenic peptidyl-pNA substrates and fluorogenic peptidyl-AMC, peptidyl-AFC, and peptidyl-MCA substrates. Exemplary Factor C substrates include, but are not limited to, N-t-Boc-DPR-AMC, N-t-Boc-VPR-MCA, N-t-Boc-VPR-AMC, Mu-VPR-AFC and Boc-VPR-pNA.

In various embodiments, rFC provided by the present invention exhibits the enzymatic activity of horseshoe crab Factor C having the amino acid sequence of SEQ ID NO: 4, more specifically the hydrolytic activity of horseshoe crab Factor C having the amino acid sequence of SEQ ID NO: 4, still more specifically the proteolytic activity of horseshoe crab Factor C having the amino acid sequence of SEQ ID NO: 4, and even more specifically the serine protease activity of horseshoe crab Factor C having the amino acid sequence of SEQ ID NO: 4.

Two-Chain Zymogen Form of Factor C

The Factor C of a horseshoe crab in its zymogen form is known to comprise a heavy (H) chain and a light (L) chain (so-called two-chain form). The recombinant Factor C of the present invention is also produced in the two-chain zymogen form. Specifically, the zymogen Factor C obtained from the methods provided by the present invention also comprises an H chain and an L chain. Therefore, the terms "Factor C of the present invention" and "zymogen Factor C of the present invention" may be used interchangeably, as mentioned herein above. Alternatively, the "zymogen (recombinant) Factor C of the present invention" may be designated as "proenzyme (recombinant) Factor C of the present invention". In any event, the recombinant Factor C directly obtained from a method of the present invention is characterized by the two-chain zymogen form comprising a heavy (H) chain and a light (L) chain.

The molecular weight of the Factor C protein of SEQ ID NO: 4 calculated on the basis of the primary amino acid sequence is 110 kDa (109.7 kDa). The scope of the present invention encompasses embodiments, in which the recombinant Factor C of the present invention has a modified primary amino acid sequence, e.g., a truncation at the N- or C-terminus. In such cases the molecular weight calculated on the basis of the primary sequence is changed. Therefore, calculated on the basis of the primary amino acid sequence, the scope of the present invention encompasses recombinant Factor C proteins having any molecular weight in the range between 90 to 130 kDa, preferably any molecular weight in the range between 95 to 125 kDa, more preferably any molecular weight in the range between 100 to 120 kDa, and still more preferably any molecular weight in the range between 105 to 115 kDa. Even more preferably, the recombinant Factor C protein of the present invention has a molecular weight in the range of 108 to 112 kDa, calculated on the basis of the primary amino acid sequence.

Surprisingly, the molecular weight of the zymogen form of Factor C as determined by SDS-PAGE turned out to be lower than the molecular weight calculated on the basis of the primary amino acid sequence. In particular, the zymogen form of Factor C produced by a method according to the present invention has a molecular weight of 102 kDa as determined by SDS-PAGE under non-reducing conditions. Furthermore, the zymogen form of Factor C produced by a method according to the present invention has a molecular weight of 106 kDa (including glycosylation) as determined by SDS-PAGE under reducing conditions, resulting from a molecular weight of 69 kDa determined for the H-chain, and a molecular weight of 37 kDa determined for the L-chain. Therefore, the present invention encompasses recombinant Factor C proteins having a molecular weight of about 102 kDa as determined by SDS-PAGE under non-reducing conditions, and recombinant Factor C proteins having a molecular weight of about 106 kDa (including glycosylation) as determined by SDS-PAGE under reducing conditions.

Upon activation of Factor C in the presence of endotoxin, chymotrypsin or lipid A (autocatalytic conversion of Factor C to the activated form), a cleavage in the L chain occurs, resulting in the occurrence of two new fragments, a B chain and an A chain.

Therefore, the recombinant Factor C of the present invention is further characterized in that activation of the zymogen form directly obtained from a method of the present invention by endotoxin, chymotrypsin or lipid A (autocatalytic conversion of Factor C to the activated form) results in activated Factor C comprising a B chain and an A chain due to cleavage of the L chain of the zymogen Factor C.

Vectors and Plasmids

In various embodiments, the polynucleotide encoding a heterologous horseshoe crab Factor C protein according to the present invention is comprised by a nucleic acid molecule, preferably a vector, which is introduced into the parasitic protozoan host cell. In other words, in various embodiments, the polynucleotide encoding a heterologous horseshoe crab Factor C protein according to the present invention is incorporated into a vector or a plasmid. In various embodiments, two or more such vectors or plasmids are used. In various embodiments, the vector or plasmid is a linear vector or a linear plasmid. In various further embodiments, the vector or plasmid may be a circular vector or circular plasmid.

The present invention provides a vector or plasmid comprising a heterologous polynucleotide used in the present invention, i.e., a heterologous polynucleotide encoding a heterologous Factor C protein from a horseshoe crab. In various embodiments, the heterologous polynucleotide is flanked by 5' and 3' UTRs (untranslated or non-translated regions) of an actively transcribed gene of a kinetoplastid parasitic protozoan. Preferably, the heterologous polynucleotide encoding the heterologous Factor C protein is flanked by 5' and 3' UTRs of an actively transcribed gene of a member of the order Trypanosomatida, more preferably by 5' and 3' UTRs of an actively transcribed gene of a member of the genus *Leishmania*, and still more preferably by 5' and 3' UTRs of an actively transcribed gene of *Leishmania tarentolae*.

In various embodiments, the vector or plasmid of the present invention comprises a promoter, which is located upstream of the heterologous polynucleotide.

In various embodiments, the vector or plasmid of the present invention comprises a promoter, which is located upstream of the heterologous polynucleotide, in addition to the 3' and 5' UTRs.

In various embodiments, the vector or plasmid provided by the present invention comprises one or more signal sequences for efficient secretion, splicing, and/or polyadenylation of the heterologous Factor C protein resulting from expression of the heterologous polynucleotide in the protozoan host cell. In various embodiments, the signal sequence is derived from a kinetoplastid parasitic protozoan. Preferably, the signal sequence is derived from a member of the order Trypanosomatida, more preferably from a member of the genus *Leishmania*, and still more preferably from *Leishmania tarentolae*.

Most preferably, the signal sequence has the amino acid sequence of SEQ ID NO: 5. Also disclosed herein are variants like fragments and/or functional derivatives of said signal sequences, in particular of the signal sequence of SEQ ID NO: 5.

In various embodiments, the vector or plasmid provided by the present invention comprises one or more selectable marker genes.

The present invention provides the use of the vector or plasmid provided by the present invention for delivery of a heterologous polynucleotide encoding a heterologous Factor C protein from a horseshoe crab into a protozoan host cell of the present invention. Preferably, the delivery is transfection of the protozoan host cell.

The scope of the present invention encompasses the use of the vector or plasmid provided by the present invention in any expression system described herein.

The transfection of the host cell species may be conducted by using amounts of DNA ranging between 1-100 μg. The selection may be performed with adequate plating techniques and conditions for an antibiotic selection, or by using any dilution technique. Transfection efficiency ranges broadly depending on the species chosen, being the highest for *Leishmania* species.

In various embodiments, a single cell can contain and/or maintain several expression constructs. Preferably, all of the several expression constructs carry different selection markers. Levels of expression vary significantly depending on the host and construct chosen, with episomal plasmids being on the low end of the scale but nevertheless able to generate recombinant protein up to 1% of total cellular protein.

The experimental results provided herein show clearly that a kinetoplastid *trypanosoma* host cell is capable of expressing a recombinant heterologous horseshoe crab Factor C protein, which can be activated by endotoxin, chymotrypsin or lipid A to become an active enyzme. It is understood that this ability is not limited to members of the order Trypanosomatida (kinetoplastid trypanosomas), but rather is a characteristic of kinetoplastid parasitic protozoan as a whole. Those of skill in the art will recognize that kinetoplastid *trypanosoma* other than members of the genus *Leishmania* can also be used for the recombinant expression of heterologous Factor C.

In various embodiments, the vector or plasmid of the present invention further comprises a nucleic acid sequence coding for one or more proteins to be fused with the Factor C protein produced by a method of the present invention. These embodiments provide for the production of fusion proteins or chimeric proteins of the Factor C protein by the methods of the present invention.

The scope of the present invention encompasses vectors and plasmids, which comprise one or more nucleic acid sequences, which code for one or more recombinant Factor C proteins.

Methods for Producing Factor C

The present invention provides a method for producing Factor C from a horseshoe crab, the method comprising the steps of (a) culturing cells of a parasitic protozoan of the present invention under conditions such that the cells of the parasitic protozoan express the Factor C encoded by the polynucleotide, and (b) recovering the Factor C produced in step (a) from the cell culture. The cells used in the methods for producing horseshoe crab Factor C according the present invention are host cells as described herein. Therefore, it is clear that the host cells used in the methods for producing horseshoe crab Factor C according the present invention comprise a polynucleotide encoding horseshoe crab Factor C as described herein.

In various embodiments, the method for producing horseshoe crab Factor C according the present invention comprises a step of transfection of a parasitic protozoan host cell with a vector or plasmid of the present invention. Obviously, such a step precedes the step of culturing the host cell under conditions such that the recombinant Factor C is expressed. Preferably, the parasitic protozoan host cell is a kinetoplastid parasitic protozoan host cell. More preferably, the kinetoplastid parasitic protozoan host cell is a digenetic trypanosomatid (i.e., a digenetic member of the order Trypanosomatida). Still more preferably, the parasitic protozoan host cell is a cell of the order Trypanosomatida. Even more preferably, the parasitic protozoan host cell is a cell of the genus *Leishmania*. Most preferably, the parasitic protozoan host cell is *Leishmania* tarentolae.

In various embodiments, the method for producing horseshoe crab Factor C protein in a host cell or expression system according to the present invention comprises culturing a stable transfected host cell of the present invention in/on a selection medium for constitutive heterologous gene expression, wherein the stable transfected host cell comprises (a) a DNA sequence coding for a gene of a selectable marker and (b) a heterologous DNA sequence coding for horseshoe crab Factor C protein operably linked and integrated into the actively transcribed gene.

In various embodiments, the method for producing horseshoe crab Factor C protein in a host cell or expression system according to the present invention comprises culturing a stable transfected host cell of the present invention in/on a selection medium for constitutive heterologous gene expression, wherein the stable transfected host cell comprises (a) a DNA sequence coding for a selectable marker gene and (b) a heterologous DNA sequence coding for horseshoe crab Factor C protein operably linked into an episomally maintained plasmid DNA with an active promoter.

In various embodiments, the method for producing horseshoe crab Factor C protein in a host cell or expression system according to the present invention comprises culturing a stable transfected host cell of the present, wherein the stable transfected host cell comprises: (a) a DNA sequence coding for a heterologous RNA polymerase, integrated into an actively transcribed gene cluster, (b) a DNA sequence coding for a selectable marker integrated into an actively transcribed gene cluster, (c) a DNA sequence coding for a transcription repressor gene integrated into an actively transcribed gene cluster, and (d) a heterologous DNA sequence coding for horseshoe crab Factor C protein prefaced with the heterologous RNA polymerase promoter and a repressor responsive element, and wherein the stable transfected host cell is cultured with a selectable marker and the expression of the heterologous gene is induced with an inhibitor of the heterologous repressor.

The scope of the present invention encompasses embodiments of the method for producing Factor C according to the present invention, in which the recombinant horseshoe crab Factor C is accumulated within the host cell. The scope of the present invention also encompasses embodiments of the method for producing Factor C according to the present invention, in which the recombinant horseshoe crab Factor C is accumulated in the cell culture medium due to secretion of the expressed protein. Therefore, in various embodiments, the step of recovering the Factor C produced in step (a) from the cell culture means recovering the Factor C from the host cells, in which the expressed Factor C protein is accumulated. Recovering the Factor C from the host cells, in which the expressed Factor C protein is accumulated, includes, but is not limited to, a step of lysis of the host cells. Exemplary techniques for cell lysis include, but are not limited to, sonication, French press, and enzymatic lysis. Recovering the Factor C from the host cells, in which the expressed Factor C protein is accumulated, may include a separate step of extraction of the expressed Factor C protein after lysis of the host cell.

In various other embodiments, the step of recovering the Factor C produced in step (a) from the cell culture means recovering the Factor C from the cell culture medium, in which the Factor C is accumulated in the cell culture medium due to secretion of the expressed protein. Recovering the Factor C from the cell culture medium, in which the Factor C protein is accumulated due to secretion of the expressed protein, may further include a separate step of extraction of the expressed Factor C protein from the cell culture medium.

In various embodiments, the step of recovering the Factor C produced in step (a) from the cell culture means recovering the Factor C from the host cells and the cell culture medium at the same time. Here, the step of recovering the Factor C includes, but is not limited to, a step of lysis of the host cells.

In various embodiments, the step of recovering the Factor C protein described above may be considered as a step of isolating the Factor C protein from the cell culture, in particular from the host cells and the cell culture medium, respectively.

In various embodiments, the Factor C directly obtained from a method according to the present invention may be considered as purified Factor C, which is directly applicable for endotoxin detection and/or endotoxin removal. Nevertheless, in various embodiments the method for producing Factor C according to the present invention may comprise a separate step of purifying the Factor C directly obtained from the production process. Preferably, the method for producing Factor C according to the present invention may comprise a step of purifying the Factor C by chromatographic means. Exemplary chromatographic means include, but are not limited to, ion exchange chromatography, gel filtration, hydrophobic interaction chromatography, reversed phase chromatography, and affinity chromatography. Clearly, such a separate step of purifying Factor C protein by chromatographic means follows any step of recovering/isolating the Factor C protein as described above.

In various embodiments, the method for producing Factor C according to the present invention may comprise a step of concentrating and/or stabilizing the Factor C protein obtained after recovery of the Factor C protein. In various embodiments, the method for producing Factor C according to the present invention may comprise a step of concentrating and/or stabilizing the Factor C protein obtained after purification of the Factor C protein by chromatographic means. The step of stabilizing Factor C protein may include the use of a protein stabilizing agent. Exemplary protein stabilizing agents include, but are not limited to, reducing agents, high mono- or bivalent salt concentrations, hydrophobic additives, amphiphilic additives, and glycerol. In various embodiments, the step of concentrating Factor C protein includes concentration of the culture supernatant resulting from the production process, i.e., the concentration step is performed prior to the step of recovery/isolation as described above. In various other embodiments, the step of concentrating Factor C protein includes concentration of the Factor C protein solution, which is obtained after performing the step of recovery/isolation of the Factor C protein as described herein above, i.e., the concentration step is performed subsequent to the step of recovery/isolation as described above. Means and methods for concentrating Factor C protein include, but are not limited to, filtration, chromatographic capture and elution, and lyophilization.

The Factor C protein of a horseshoe crab produced by a method of the present invention has been demonstrated to be enzymatically active upon binding to endotoxin or chymotrypsin, as described in Example 4. The fact that the Factor C so produced retains the bioactivity of having Factor C-like enzymatic activity is a characteristic technical feature of the recombinant Factor C provided by the present invention because many attempts in the art to produce enzymatically active Factor C in various host cells have failed, as discussed herein above. The present inventors have surprisingly found that recombinant production of Factor C from horseshoe crabs in a protozoan host cell provides for a Factor C protein, which is enzymatically active upon activation by endotoxin (or chymotrypsin or lipid A). This could not have been expected from the teachings in the prior art, according to which the production of enzymatically active Factor C protein in prokaryotes and lower eukaryotic did not provide an enzymatically active Factor, and according to which higher eukaryotic expression systems should be used for producing rFC with full biological activity rather than a prokaryotic or simple eukaryotic expression system like yeast. As described in the background section, the successful use of insect cells has led to this teaching, in connection with the knowledge that insect cells more closely resemble the cells of the horseshoe crab than yeast cells in their physiology and biochemistry. Thus, it was considered in the art that recombinant Factor C is to be produced in cells, which more closely resemble the protein as purified from its natural source, i.e., horseshoe crabs, and retain the bioactivity of having serine protease activity after activated by endotoxin.

The scope of the present invention encompasses production of recombinant horseshoe Factor C in fermenter cultures based on the means and methods for producing recombinant Factor C described herein. The scope of the present invention also encompasses a fermentation production of recombinant horseshoe Factor C on an industrial scale based on the means and methods for producing recombinant Factor C described herein. The scope of the present invention encompasses the use of any kind of fermenter, including laboratory-scale fermenters and industrial scale fermenters. In the fermentation production according to the present invention, the concentration of, inter alia, the carbon source(s) is preferably controlled during the culture to a concentration such that substantially no adverse effects are caused on the productivity of the recombinant Factor C protein.

Factor C Produced by Methods of the Present Invention

Factor C produced by a method of the present invention encompasses Factor C protein having the amino acid sequence of Factor C as found in its natural source, i.e., as obtainable from horseshoe crabs, as well as variants thereof as described herein. Similarly, Factor C produced by a method of the present invention encompasses Factor C protein encoded by a nucleic acid sequence, which is identical with the nucleic acid sequence encoding Factor C as found in its natural source, i.e., as obtainable from horseshoe crabs, as well as variants thereof as described herein. In any event, Factor C protein produced by a method of the present invention shows Factor C-like enzymatic activity upon activation with endotoxin (or chymotrypsin or lipid A).

In the present invention, the term "Factor C produced by a method of the present invention" encompasses "Factor C obtained (or obtainable) from a method of the present invention". Said terms may be used interchangeably.

The production of Factor C from horseshoe crab in a protozoan host cell, in particular in a trypanosomatid host cell (i.e., a host cell of the order Trypanosomatida) exemplified by cells of the genus *Leishmania*, provides for a specific glycosylation of Factor C, which is different from the glycosylation pattern provided by the expression of Factor C in prokaryotic organisms, yeast, and higher eukaryotic expression systems like insect cells. Therefore, the Factor C obtained from the method of the present invention is structurally different from Factor C protein obtained from methods described in the art. Therefore, the method for producing Factor C provided by the present invention provides for a product, i.e., recombinant Factor C, which as such is novel over Factor C described in the prior art. The present invention therefore provides a novel Factor C protein, which is obtainable by a method for producing horseshoe crab Factor C according to the present invention.

As used herein, an equivalent wording for "obtainable" is represented by the terms "obtained" or "directly obtained".

Preferably, the Factor C produced by a method of the present invention has an amino acid sequence which is substantially identical with the amino acid sequence of Factor C from *Tachypleus tridentatus*, more preferably the Factor C produced by a method of the present invention comprises the amino acid sequence of SEQ ID NO: 4. The recombinant production of Factor C from *Tachypleus tridentatus* has not been described before. In particular, the production of Factor C from *Tachypleus tridentatus* in a parasitic protozoan host, specifically in a trypanosomatid host cell (i.e., a host cell of the order Trypanosomatida) exemplified by cells of the genus *Leishmania*, has not been described before.

Recombinant Factor C protein of the present invention can be isolated and purified from a protozoan host cell of the present invention containing or expressing the recombinant Factor C protein by techniques known in the art including, but not limited to, lysis, chromatography, filtration, and centrifugation. The same applies with respect to the isolation and purification of recombinant Factor C of the present invention from cell culture medium in case the expressed protein is secreted and accumulated in the cell culture medium. As explained herein above, in various embodiments, Factor C directly obtained from a method of the present invention may be considered as purified Factor C, i.e., without the application of specific purification of Factor C by chromatographic means. In particular, for certain applications of Factor C the protein may be isolated from the host cell (in case the Factor C protein is accumulated intracellularly) or from the cell culture medium (in case the Factor C protein is secreted into the cell culture medium) without performing a separate purification step involving chromatographic means. In various embodiments, even the cell culture medium containing secreted and accumulated Factor C protein may be used for certain applications of endotoxin detection or endotoxin removal. The scope of the present invention encompasses the use of the cell culture medium containing the Factor C, wherein the cell culture medium has been concentrated and/or the Factor C protein in the cell culture medium has been stabilized prior to application of the cell culture medium. Means and methods for concentrating the cell culture medium include, but are not limited to, filtration, chromatographic capture and elution, and lyophilization. Furthermore, the Factor C protein contained in the cell culture medium may include the use of a protein stabilizing agent. Exemplary protein stabilizing agents include, but are not limited to, reducing agents, high mono- and bivalent salt concentrations, hydrophobic additives, amphiphilic additives and glycerol.

In various embodiments, the isolated and/or purified recombinant Factor C protein produced by the present invention is labeled. Preferably, the label is selected from the group consisting of an enzyme label, a radioisotope, a fluorescent label, and biotin.

Also encompassed by the present invention is recombinant Factor C produced by a method of the present invention, which is combined with part(s) of the constant domain of an immunoglobulin (IgG), resulting in a chimeric Factor C provided by the present invention. These fusion proteins may facilitate isolation and/or purification of Factor C provided according to the methods of the present invention.

The scope of the present invention encompasses fusion proteins of recombinant Factor C, which can be produced by methods for producing Factor C protein of the present invention.

The present invention further provides chimeric proteins comprising Factor C produced according to a method of the present invention and one or more heterologous proteins.

As described herein above, the recombinant Factor C of the present invention is produced as a zymogen (or proenzyme), which is inducible by the presence of trace levels of endotoxin. Specifically, the Factor C obtained by a method of the present invention is (auto-)catalytically converted into its active form in the presence of endotoxin. Factor C produced by a method of the present invention may be protected from activation by endotoxin and autocatalytic cleavage of the L chain by contacting the Factor C produced with a stabilizing agent like, e.g., DMSO, 2-propanol, or protease inhibitors, and, optionally, a chelating agent. If the Factor C protein upon expression is accumulated intracellularly within a protozoan host cell according to the present invention, said contacting can be performed by lysing the host cells in the presence of DMSO and, optionally, a chelating agent. If the Factor C protein of the present invention is secreted into the cell culture medium, said contacting can be performed by adding DMSO and, optionally, a chelating agent, to the cell culture medium prior to isolating and/or further purifying the Factor C protein. Of course, in various embodiments said contacting can be performed by adding DMSO and, optionally, a chelating agent, to the cell culture medium after isolating and/or further purifying the Factor C protein. Basically DMSO can be added to solutions which are used during the isolation and/or purification process. Even greater protection of the Factor C produced by a method according to the present invention is achieved by also adding to the isolation/purification solution an agent effective for chelating divalent metal ions.

In various embodiments, the Factor C protein of the present invention is accumulated intracellularly within a protozoan host cell according to the present invention. In various other embodiments, the Factor C protein of the present invention is accumulated in the cell culture medium of the protozoan host cell culture according to the present invention.

The accumulation of the Factor C protein in the cell culture medium is normally due to secretion of the expressed protein. However, the scope of the present invention also encompasses embodiments, in which the accumulation of the Factor C protein in the cell culture medium is due to lysis of the host cells, in which the Factor C protein was first accumulated intracellulary. Exemplary techniques for cell lysis performed after expression and intracellular accumulation of the Factor C protein include, but are not limited to, sonication, French press, and enzymatic lysis.

Affinity tags are appended to proteins so that they can be purified from their crude biological source using an affinity technique. The scope of the present invention encompasses Factor C produced by a method of the present invention, wherein the Factor C produced comprises an affinity tag for purification. Such purification tags include, but are not limited to, HIS, CBP, CYD (covalent yet dissociable NorpD peptide), Strep II, FLAG, and HPC (heavy chain of protein C) amino acid and peptide tags, as well as the GST and MBP protein fusion tag systems.

The present invention also comprises Factor C protein produced by the present invention carrying a chemical tag. An exemplary chemical tag is biotin, which provides for purification by tight binding to streptavidin-agarose or streptavidin-beads. Biotinylation of Factor C of the present invention also includes biotinylated Factor C for immobilization of the Factor C onto surfaces. The biotin tag can be used in affinity chromatography with a column that has avidin (also streptavidin or neutravidin) bound to it. The biotin tag can also be used for detection of Factor C via anti-biotin antibodies or avidin/streptavidin-tagged detection strategies such as enzyme reporters (e.g., horseradish peroxidase, alkaline phosphatase) or fluorescent probes. This can be useful in immunoanalytical methods including, but not limited to, ELISA assays.

Purified Factor C

As described herein, the present invention provides Factor C produced by a method according to the present invention.

The Factor C obtained from a method according to the present invention can be directly applied to methods for endotoxin detection or endotoxin removal without any separate purification by chromatographic means. Therefore, as described herein already elsewhere, the Factor C directly obtained from a method according to the present invention may thus be considered as purified Factor C. The present invention also encompasses Factor C, which is further purified by chromatographic means, i.e., the Factor C produced by a method according to the present invention or directly obtained from a method according to the present invention is further purified by chromatographic means. The application of chromatographic means includes, but is not limited to, ion exchange chromatography, gel filtration, hydrophobic interaction chromatography, reversed phase chromatography, and affinity chromatography.

In various embodiments, purified Factor C according to the present invention includes, but is not limited to, isolated, concentrated and/or stabilized Factor C. The isolated Factor C includes, but is not limited to, Factor C isolated from the cell culture or the cell culture medium obtained from culturing a protozoan host cell for producing Factor C according to the present invention. The concentrated Factor C includes, but is not limited to, Factor C concentrated from the cell culture or the cell culture medium obtained from culturing a protozoan host cell for producing Factor C according to the present invention. Means and methods for concentrating the Factor accordingly include, but are not limited to, filtration, chromatographic capture and elution, and lyophilization. The stabilized Factor C includes, but is not limited to, Factor C stabilized by a protein stabilizing agent. Exemplary protein stabilizing agents include, but are not limited to, reducing agents, high mono- and bivalent salt concentrations, hydrophobic additives, amphiphilic additives and glycerol.

In various embodiments, purified Factor C according to the present invention includes, but is not limited to, intermediately purified Factor C, which means Factor C, which is purified from most of the bulk impurities such as other proteins and nucleic acids.

In various embodiments, purified Factor C according to the present invention includes, but is not limited to, high purity Factor C, which means Factor C purified from any remaining trace impurities or closely related substances.

In various embodiments, the Factor C provided by the present invention, or produced by a method of the present invention, has a purity of at least 75% or at least 80%, i.e., Factor C constitutes at least 75% or at least 80% of the total protein. In various embodiments, the Factor C provided by the present invention, or produced by a method of the present invention, has a purity of at least 85% or at least 90%, i.e., Factor C constitutes at least 85% or at least 90% of the total protein. In various embodiments, the Factor C provided by the present invention, or produced by a method of the present invention, has a purity of at least 95% or at least 96%, i.e., Factor C constitutes at least 95% or at least 96% of the total protein. In various embodiments, the Factor C provided by the present invention, or produced by a method of the present invention, has a purity of at least 97% or at least 98%, i.e., Factor C constitutes at least 97% or at least 98% of the total protein. In various embodiments, the Factor C provided by the present invention, or produced by a method of the present invention, has a purity of at least 99% or even 100%, i.e., Factor C constitutes at least 99% or even 100% of the total protein.

Antibodies

The present invention also provides an antibody or fragment thereof that binds specifically to a Factor C protein or fragment thereof provided by the present invention or obtained from a method of the present invention. Preferably, the antibody specifically binds to full-length Factor C having the amino acid sequence of SEQ ID NO: 2 or SEQ ID NO: 4.

In various embodiments, the antibody of the present invention is selected from the group consisting of a monoclonal antibody, a polyclonal antibody, a chimeric antibody, a Fab fragment, a F(ab')$_2$ fragment, and a scFv fragment. In various embodiments, the antibody according to the present invention is labeled. Preferably, the label is selected from the group consisting of an enzyme label, a radioisotope, a fluorescent label, and biotin. The Factor C protein of the present invention can be used to raise polyclonal and monoclonal antibodies provided by the present invention. The antibodies of the present invention may be prepared by any of a variety of methods available in the art and known to the one of ordinary skill in the art.

The antibody fragments provided by the present invention, whether attached to other sequences or not, can also include insertions, deletions, substitutions, or other selected modifications of particular regions or specific amino acids residues, provided that the activity of the antibody fragment is not significantly altered or impaired compared to the non-modified antibody or antibody fragment. These modifications can provide for some additional property, such as to remove/add amino acids capable of disulfide bonding. In any case, antibody fragments according to the present invention must possess a bioactive property, such as specific binding to its cognate antigen.

Functional or active regions of the antibodies or antibody fragments of the present invention may be identified by mutagenesis of a specific region of the protein, followed by expression and testing of the expressed polypeptide. Such methods are readily apparent to a skilled practitioner in the art and can include site-specific mutagenesis of the nucleic acid encoding the antibody or antibody fragment.

Compositions and Solutions

The present invention provides compositions comprising recombinant Factor C protein produced according to a method of the present invention. The present invention also provides a composition comprising a polynucleotide or nucleic acid molecule of the present invention. The present invention also provides a composition comprising a vector or plasmid of the present invention. The present invention further provides a composition comprising a parasitic protozoan host cell according to the present invention. The present invention further provides a composition comprising a fusion protein or a chimeric protein according to the present invention.

In various embodiments, a composition according to the present invention is a diagnostic composition.

In various embodiments, a composition according to the present invention is a composition for detecting endotoxin, preferably for detecting endotoxin in a sample. In various embodiments, the sample is an environmental sample. In various embodiments, the sample is a biological sample. In various embodiments, the sample is a test sample, preferably a biological or environmental test sample. Preferably, the biological sample or biological test sample is a biological sample or biological test sample obtained from a mammal. Preferably, the mammal is a human being. The scope of the present invention encompasses endotoxin detection in a sample obtained from animals including, but not limited to, dogs, cats, pigs, horses, birds, and reptiles.

The present invention provides solutions, preferably diagnostic solutions, comprising recombinant Factor C protein of the present invention. The present invention also provides solutions for removing endotoxin comprising recombinant Factor C produced according to a method of the present invention.

In various embodiments, Factor C produced by a method according to the present invention or obtained from a method of the present invention may be designated as an agent for measuring/detecting endotoxin (endotoxin-measuring/detecting agent). In various embodiments, Factor C produced by a method according to the present invention or obtained from a method of the present invention may be designated as an agent for removing endotoxin (endotoxin-removing agent).

Compositions and solutions of the present invention, which comprise Factor C of the present invention, may furthermore comprise a component other than the recombinant Factor C produced by a method of the present invention. In particular, the agent may furthermore comprise a Factor C substrate for detection, as long as the agent can be used for measurement/detection of endotoxin.

The Factor C-containing compositions and solutions of the present invention may also comprise, e.g., a pH-buffering agent and/or a salt, preferably a chelating salt. Examples of pH-buffering agents include, but are not limited to, HEPES buffer, MES buffer, and Tris buffer. Organic solvents such as alcohols, esters, ketones, and amides may also be comprised in the compositions and solutions of the present invention.

The endotoxin-measuring/detecting agent and/or endotoxin-removing agent of the present invention may be formulated in an arbitrary form including, but not limited to, a solid form, a liquid form, and a gel form. Additives may be used as formulation carriers, including, but not limited to, vehicles, binders, disintegrants, lubricants, stabilizers, correctives, and diluents, and solvents.

In various embodiments, compositions and solutions of the present invention, which comprise recombinant Factor C of the present invention, may further comprise a surfactant. Therefore, the present invention provides a reagent for detecting endotoxin, comprising a horseshoe crab Factor C protein produced according to a method of the present invention or obtained from a method of the present invention, and a surfactant.

In various embodiments, the surfactant is an amphoteric surfactant. In various other embodiments, the surfactant is an anionic surfactant or a cationic surfactant. In various other embodiments, the surfactant is a non-ionic surfactant. Preferably, the surfactant is selected from the group consisting of ZWITTERGENT 3-14, Triton X-100, Triton X-114, octyl-beta-D-thioglucoside, Genapol C-100, Tween 20, and Tween 80. Preferably, the surfactant is present in a composition or solution of the present invention at a concentration of 0.001 to 0.5%, more preferably at a concentration of 0.001 to 0.025%, still more preferably at a concentration of 0.001 to 0.01%. In various embodiments, the surfactant is present in a composition or solution of the present invention at a concentration of 0.004 to 0.006%.

The Factor C protein of the present invention may be used for measuring/detecting endotoxin as it is, or may be used after being diluted, dispersed, or dissolved in water, physiological saline, buffer, or the like. "Factor C protein as it is" encompasses any form of Factor C protein directly obtained from a method of the present invention, including isolated, concentrated and/or purified Factor C obtained from a method of the present invention. The scope of the present invention also encompasses "Factor C protein as it is" obtained after being purified by chromatographic means. Such embodiments are within the scope of the present invention.

Methods for Endotoxin Detection

The recombinant Factor C provided by the present invention forms the basis of an endotoxin diagnostic assay for high throughput screens of endotoxin. The endotoxin-activated recombinant Factor C zymogen catalytically hydrolyses synthetic substrates to form measurable products, thus quantifying the endotoxin.

The present invention provides the use of Factor C protein produced by methods for producing Factor C according to the present invention in a method for endotoxin detection. In various embodiments, Factor C of the present invention is used in a method for endotoxin detection comprising contacting a sample, preferably a test sample, to be assayed for the presence of endotoxin (LPS) or lipid A with recombinant Factor C according to the invention, and measuring enzymatic activity (i.e., serine protease activity) of the recombinant Factor C. The enzymatic activity of the recombinant Factor C reflects its activation due to binding of endotoxin or lipid A, or of another endotoxin known in the art to bind to Factor C of a horseshoe crab. The Factor C enzymatic activity (in particular the serine protease activity) is conveniently measured by any known method known in the art, but is preferably measured by a chromogenic or fluorogenic method. Such methods comprise measuring the formation of a product, which results from cleavage of a Factor C substrate by the protease activity of the recombinant Factor C. The measurement is based on a change in colour (in case of a chromogenic substrate) or fluorescence emission (in case of a fluorogenic substrate) resulting from cleavage of the substrate. The scope of the present invention encompasses the use of chromogenic and fluorogenic Factor C substrates, which include, but are not limited to, chromogenic peptidyl-pNA substrates and fluorogenic peptidyl-AMC, peptidyl-AFC, and peptidyl-MCA substrates. Preferred substrates for such a chromogenic or fluorogenic assay are N-t-Boc-VPR-MCA, N-t-Boc-VPR-AMC, Mu-VPR-AFC and Boc-VPR-pNA.

Further embodiments of the present invention include immunologic methods for assaying the presence of endotoxin or lipid A in a sample, preferably a test sample. These methods of the present invention are based on the specific binding of an antibody to recombinant Factor C, followed by detection and/or quantitation of the Factor C-antibody complex. In a preferred embodiment, the sample to be assayed is contacted with an immobilized antibody that specifically binds to endotoxin or lipid A. The immobilized ligand (i.e., immobilized endotoxin or lipid A) is then contacted with recombinant Factor C according to the present invention, resulting in an immobilized recombinant Factor C (rFC). The immobilized rFC is then contacted with a second antibody specifically binding to the immobilized rFC. The presence and/or the amount of the immobilized complex, which comprises the rFC bound to the second antibody, can then be determined by any technique known in the art, e.g., by applying a third antibody that specifically binds the second antibody, e.g., through the Fc portion of the antibody. In an alternative embodiment, instead of applying the second antibody the enzymatic activity of the immobilized rFC is measured.

In another embodiment of the present invention, the specific binding of endotoxin or lipid A to rFC of the present invention is employed in commercially available assays, e.g., the BIACORE™ assay (Pharmacia Biotech). By immobilizing the rFC on the substrate plate of such apparatuses, the presence of endotoxin or lipid A in a sample can be detected. The one of ordinary skill in the art is able to optimize the amount of the rFC to be immobilized for a given load of endotoxin in a sample.

In various embodiments, the method for detecting endotoxin according to the present invention is performed on a test sample, preferably a test sample obtained from a mammal. Preferably, the mammal is a human being. The scope of the present invention also encompasses endotoxin detection in a test sample obtained from animals including, but not limited to, dogs, cats, pigs, horses, birds, and reptiles.

In various embodiments, the method of the present invention for endotoxin detection comprises the use of an endotoxin-selective, pre-coated solid support. In particular, the selective capture of endotoxin (LPS) is achieved using a phage-derived receptor protein which is directed to the inner core part (i.e., the inner core oligosaccharide) or the lipid A part of LPS. The inner core structure of LPS, together with the lipid A part, is a highly conserved structure. The outer core structure is slightly variable and the O-antigen is highly heterogenous. Preferably, the phage-derived receptor protein to be used in the present invention is exhibiting high-affinity and high specificity for the conserved regions of endotoxin. The highly conserved regions of endotoxin bound by the said phage-derived receptor protein encompass both the core region and lipid A. Therefore, the said phage-derived receptor protein binds to the inner core region (i.e., the inner core oligosaccharide) and/or lipid A. In various embodiments, the said phage-derived receptor protein is a bacteriophage tail protein, a bacteriophage head protein of a bacteriophage with tail, or a bacteriophage coat protein of a bacteriophage without tail. Preferably, the said phage-derived receptor protein is a bacteriophage tail protein. Preferably, the bacteriophage tail protein is a protein of the short bacteriophage tail fiber. In various embodiments, the short bacteriophage tail fiber is selected from K3, T2, T4, Ox2, RB32-33, AR1, PP01 and RB69. In various embodiments, the bacteriophage tail protein is modified for the detection of endotoxin according to the present invention. In various embodiments, the bacteriophage tail protein may be coupled to an active protein.

After binding of sample endotoxin (LPS) to the solid support pre-coated with said phage-derived receptor protein, the original sample matrix is washed off, thereby eliminating components which potentially interfere with the detection reaction. Subsequently, endotoxin is detected by Factor C of the present invention in a process, which includes reaction of Factor C with a Factor C substrate. In various embodiments, the substrate is a chromogenic or a fluorogenic substrate.

In various embodiments, the solid support to be pre-coated with the phage-derived receptor protein is a microtiter plate, a bead (e.g., a silica bead or an organic polymer bead), a foil or a membrane. Thus, the method of the present invention for endotoxin detection including the use of an endotoxin-selective, pre-coated solid support, comprises three steps: the first step comprises binding of sample endotoxin (i.e., endotoxin contained in a sample) to a solid support, which is pre-coated with a phage-derived receptor protein exhibiting high-affinity and high specificity for the conserved core region of LPS. The first step provides for immobilization of sample endotoxin. The second step is a washing step for washing off the original sample matrix. The third step comprises detection of the immobilized endotoxin by a Factor C protein of the present invention. The third step includes the reaction of Factor C with a substrate for Factor C, which results in a detectable signal. In various embodiments, the Factor C substrate is added after the immobilized endotoxin has been contacted with Factor C protein. In various embodiments, the Factor C substrate is already present in the assay before Factor C protein is added. The specific technical effect of this three-step assay format is that it has a detection range from 0.05 EU/ml up to 500 EU/ml. Furthermore, this assay format exhibits clear advantages over the established homogeneous detection methods, including: fewer false-positive results induced by, e.g., 1-glucan, proteases or phospholipids, fewer false-negative results caused by inhibitory constituents of the sample, fewer invalid results necessitating re-testing, less interference in complex samples, and therefore higher sensitivity, and broad dynamic range.

The three-step assay format provided by the present invention is particularly useful in the detection of endotoxin in human body fluids, such as blood, serum and plasma. Preferably, the above-described three-step assay is for assaying clinical biological samples. The assay is not directly applied on a patient, but is instead applied on a test sample obtained from a patient.

In various embodiments, the present invention provides a method for detecting endotoxin in a sample, comprising the steps of (i) contacting a sample to be assayed with an endotoxin-detecting agent of the present invention to form a mixture of the test sample and the endotoxin-detecting agent, (ii) adding a Factor C substrate to said mixture, wherein cleavage of the Factor C substrate generates a detectable signal, and (iii) assaying said mixture for the presence or absence of the detectable signal, wherein an amount of the detectable signal that is increased relative to a control sample that does not contain endotoxin indicates the presence of endotoxin in the test sample.

In the endotoxin assays provided by the present invention, the Factor C substrate preferably is a chromogenic or fluorogenic Factor C substrate. In various embodiments, the Factor C substrate is a chromogenic peptidyl-pNA substrate. In various other embodiments, the Factor C substrate is a fluorogenic peptidyl-AMC, peptidyl-AFC, or peptidyl-MCA substrate. Further exemplary Factor C substrates include, but are not limited to, N-t-Boc-DPR-AMC, N-t-Boc-VPR-AMC, Mu-VPR-AFC and Boc-VPR-pNA.

In various embodiments, the present invention provides a method for detecting endotoxin in a sample, comprising the steps of (i) contacting a sample to be assayed with an endotoxin-detecting agent of the present invention and a Factor C substrate to form a mixture of the test sample, the endotoxin-detecting agent and the Factor C substrate, wherein cleavage of the Factor C substrate generates a detectable signal, and (ii) assaying said mixture for the presence or absence of the detectable signal, wherein an amount of the detectable signal that is increased relative to a control sample that does not contain endotoxin indicates the presence of endotoxin in the test sample.

The present invention also provides an assay for endotoxin comprising: (i) contacting a sample to be assayed with an immobilized antibody that specifically binds to endotoxin (LPS) or that specifically binds to lipid A, to form a complex between said antibody and endotoxin in said sample, (ii) contacting said complex with recombinant Factor C produced by a method of the present invention to form an immobilized complex comprising said antibody, endotoxin and recombinant Factor C, (iii) contacting said immobilized complex of (ii) with an antibody that specifically binds to said recombinant Factor C, and (iv) quantitating the amount of said antibody specifically bound to said recombinant Factor C.

In the present invention, terms like "method for endotoxin detection" or "method for detecting endotoxin" may be used interchangeably with the term "assay for endotoxin".

Methods for Removing Endotoxin

The present invention provides the use of Factor C protein produced by a method according to the present invention in a method for removing endotoxin. The use of Factor C of the present invention in such methods includes, but is not limited to, removal of endotoxin from water, buffers, and cell culture media. Various other embodiments pertaining to the use of Factor C of the present invention in a method for removing endotoxin include, but are not limited to, removal of endotoxin from biological and non-biological preparations, preferably biological preparations, more preferably biological preparations for animal studies, cell culture, transplantation, stem cell technologies, cell sorting, and other mammalian cell treatments. Various further embodiments pertaining to the use of Factor C of the present invention in a method for removing endotoxin include, but are not limited to, removal of endotoxin from medical equipments, medical apparatuses, cosmetics, foods and beverages.

The Factor C of the present invention can be used to produce endotoxin-free preparations, in particular endotoxin-free biological and non-biological preparations. The present invention provides the use of Factor C in a method for removing of endotoxin (LPS) from biological preparations of, e.g., proteins, antibodies, vaccines, nucleic acids, buffers and/or various other substances. Preferably, a biological preparation according to the present invention is a liquid biological preparation, more preferably an aqueous biological preparation. A liquid or aqueous biological preparation may be considered as a liquid or aqueous biological solution, or as a liquid or aqueous biological composition.

In various embodiments of the present invention, the terms "biological preparation", "biological solution" and "biological composition" may be used interchangeably.

In various embodiments, the method for removing endotoxin according to the present invention comprises the use of Factor C of the present invention immobilized to a solid support. Preferably, the solid support is a chromatography resin. The method for removing endotoxin according to the present invention can be employed in column or in batch mode, by gravity flow, or on fully automated liquid chromatography systems.

The removal of endotoxins from biological preparations is of particular importance when considering the fact that biological products for pharmaceutical use must be sufficiently free of endotoxin to enable administration to humans. Therefore, the present invention provides the use of Factor C of the present invention in a method for producing endotoxin-free preparations, in particular endotoxin-free preparations for pharmaceutical use. A preparation comprising a biological product for pharmaceutical use may directly result from a pharmaceutical process, i.e., the preparation is a pharmaceutical process preparation. Therefore, in various embodiments, the present invention provides a method for removing endotoxin from pharmaceutical process preparations comprising treating the pharmaceutical process preparation with a recombinant Factor C of the present invention. Such pharmaceutical process preparations may contain a pharmaceutical drug or a vaccine substance. In various embodiments, the pharmaceutical drug or vaccine substance comprises a polypeptide, preferably a glycoprotein. In various embodiments, the pharmaceutical drug or vaccine substance is a vaccine antigen.

Preferably, a pharmaceutical process preparation according to the present invention is a liquid pharmaceutical process preparation, more preferably an aqueous pharmaceutical process preparation. In various embodiments of the present invention, the terms "pharmaceutical process preparation" and "pharmaceutical process composition" may be used interchangeably.

The scope of the present invention also encompasses performing the method for removing endotoxin according to the present invention on any kind of a sample. In particular, the present invention provides a method for removing endotoxin or lipid A from a sample comprising: (i) contacting immobilized recombinant Factor C produced by or obtained from a method of the present invention with said sample, so that endotoxin or lipid A in said sample binds to said immobilized recombinant Factor C, and (ii) separating said immobilized recombinant Factor C, having said endotoxin or lipid A bound thereto, from said sample.

Samples

In applications comprising quantitative measurement of endotoxin, an endotoxin standard sample with a known concentration can be used in order to generate data correlating the endotoxin level and the degree of reaction of the substrate for detection (e.g., degree of coloring, fluorescence emission, and the like). This allows quantitation of endotoxin present in a sample to be assayed according to the present invention based on the correlation data obtained.

The sample to be subjected to the detection and/or removal of endotoxin according to the present invention is not particularly limited, and examples thereof include water samples, buffer samples, and samples from cell culture media. In various embodiments, the sample is a test sample. In various embodiments, the sample is a test sample of a biological preparation described herein elsewhere. In various embodiments, the sample includes, but is not limited to, a test sample from medical equipment, a medical apparatus, cosmetics, food and beverages described herein elsewhere.

In various embodiments, the sample to be subjected to the detection and/or removal of endotoxin according to the present invention is a test sample obtained from a mammal. Preferably, the test sample obtained from a mammal includes, but is not limited to, a blood sample, a serum sample or a saliva sample. Preferably, the mammal is a human.

In various embodiments, the test sample therefore is a human blood sample, a human serum sample, or a human saliva sample, preferably a human blood sample.

In various embodiments, test samples to be subjected to the detection and/or removal of endotoxin include, but are not limited to, test samples obtained from any of the following: medical water, a pharmaceutical, an infusion solution, a blood preparation. Preferably, the blood preparation is obtained from a mammal, more preferably from a human. In various embodiments, the test sample is an environmental sample.

In various embodiments, the sample to be subjected to the detection and/or removal of endotoxin according to the present invention includes, but is not limited to, a sample from a biological preparation of, e.g., proteins, antibodies, vaccines, nucleic acids, buffers and/or various other substances. In various other embodiments, the sample to be subjected to the detection and/or removal of endotoxin according to the present invention includes, but is not limited to, a sample from a pharmaceutical process preparation described herein elsewhere.

Assays and Kits

As described herein above, terms like "method for endotoxin detection" or "method for detecting endotoxin" may be used interchangeably with the term "assay for endotoxin". Therefore, the present invention provides an assay for endotoxin comprising the application of recombinant Factor C produced by a method of the present invention in accordance with the methods for endotoxin detection described herein elsewhere. Basically, an assay for endotoxin according to the present invention comprises the same method steps as a method for endotoxin detection according to the present invention.

Furthermore, the present invention provides a kit for endotoxin detection comprising a recombinant Factor C of the present invention, i.e., a Factor C produced by a method according to the present invention. Preferably, the kit further comprises instructions for a method for endotoxin detection or an assay for endotoxin of the present invention. Preferably, the instructions are in the form of a manual.

In various embodiments, the kit further comprises a surfactant, which increases the sensitivity of the endotoxin detection. The surfactant and the Factor C protein may be present in the kit in separate containers.

In various embodiments, the kit comprises one single container with a composition or solution of the present invention comprising recombinant Factor C of the present invention and a surfactant as described herein elsewhere.

In various embodiments, the surfactant contained in the kit is an amphoteric surfactant. In various other embodiments, the surfactant is an anionic surfactant or a cationic surfactant. In various other embodiments, the surfactant is a non-ionic surfactant. Preferably, the surfactant is selected from the group consisting of ZWITTERGENT 3-14, Triton X-100, Triton X-114, octyl-beta-D-thioglucoside, Genapol C-100, Tween 20, and Tween 80. Preferably, the surfactant is present in the kit at a concentration of 0.001 to 0.5%, more preferably at a concentration of 0.001 to 0.025%, still more preferably at a concentration of 0.001 to 0.01%. In various embodiments, the surfactant is present in the kit at a concentration of 0.004 to 0.006%. This includes the presence of the surfactant in a separate container or in a composition or solution of the present invention, which comprises both the recombinant Factor C of the present invention and the surfactant.

In various embodiments, the container comprising the surfactant is a container comprising a buffer, which comprises in addition the surfactant.

In various embodiments, the kit further comprises a Factor C substrate. Specifically, cleavage of the Factor C substrate by the hydrolytic activity of activated Factor C (i.e., auto-catalytically activation in the presence of endotoxin or lipid A as described herein elsewhere) generates a detectable signal. Preferably, the kit comprises a chromogenic and/or fluorogenic Factor C substrate. In various embodiments, the Factor C substrate is a chromogenic peptidyl-pNA substrate. In various other embodiments, the Factor C substrate is a fluorogenic peptidyl-AMC, peptidyl-AFC, or peptidyl-MCA substrate. Further exemplary Factor C substrates include, but are not limited to, N-t-Boc-DPR-AMC, N-t-Boc-VPR-AMC, N-t-Boc-VPR-MCA, Mu-VPR-AFC and Boc-VPR-pNA.

Process of Generating a Parasitic Protozoan Host Cell Producing Recombinant Factor C The present invention provides a process for generating a parasitic protozoan host cell that produces recombinant Factor C protein, comprising the steps of: (a) introducing a nucleic acid molecule, preferably a vector or a plasmid, comprising a polynucleotide encoding heterologous horseshoe crab Factor C into a parasitic protozoan host cell, and (b) selecting for one or more host cells produced in step (a) that express said Factor C protein. Preferably, a vector or a plasmid according to the present invention is introduced into the parasitic protozoan host cell, i.e., a vector or plasmid comprising a nucleic acid molecule encoding heterologous horseshoe crab Factor C protein. Furthermore, the parasitic protozoan host cell preferably is a kinetoplastid parasitic protozoan host cell. More preferably, the kinetoplastid parasitic protozoan host cell is a digenetic trypanosomatid (i.e., a digenetic member of the order Trypanosomatida). Still more preferably, the parasitic protozoan host cell is a cell of the order Trypanosomatida. Even more preferably, the parasitic protozoan host cell is a cell of the genus *Leishmania*. Most preferably, the parasitic protozoan host cell is *Leishmania tarentolae*.

The present invention also provides a parasitic protozoan host cell obtainable by the process for generating a parasitic protozoan host cell that produces recombinant Factor C protein described above, wherein the parasitic protozoan host cell comprises a polynucleotide encoding heterologous horseshoe crab Factor C, wherein said polynucleotide is comprised by a nucleic acid molecule, preferably a vector or a plasmid, introduced into the parasitic protozoan host cell. Preferably, the parasitic protozoan host cell comprises a vector or a plasmid according to the present invention, i.e., a vector or plasmid comprising a nucleic acid molecule encoding heterologous horseshoe crab Factor C protein. Furthermore, the parasitic protozoan host cell preferably is a kinetoplastid parasitic protozoan host cell. More preferably, the kinetoplastid parasitic protozoan host cell is a digenetic trypanosomatid (i.e., a digenetic member of the order Trypanosomatida). Still more preferably, the parasitic protozoan host cell is a cell of the order Trypanosomatida. Even more preferably, the parasitic protozoan host cell is a cell of the genus *Leishmania*. Most preferably, the parasitic protozoan host cell is *Leishmania tarentolae*.

Cell Lines

The present invention also provides stably transfected cell lines obtainable by the disclosed vectors and/or plasmids. Preferably, the transfected cell lines are cell lines obtained from stable transfection of kinetoplastid parasitic protozoan cells. More preferably, the transfected cell lines are cell lines obtained from stable transfection of cells of the order Trypanosomatida. More preferably, the transfected cell lines are cell lines obtained from stable transfection of cells of the genus *Leishmania*. Still more preferably, the transfected cell lines are cell lines obtained from stable transfection of cells of the species *Leishmania tarentolae*.

Other General Definitions

In general, whenever reference is made herein to Factor C produced according to a method of the present invention, or to "Factor C obtained according to a method of the present invention", or just to "Factor C of the present invention", such reference includes any fragments, analogs or functional derivatives of said Factor C of the present invention having Factor C-like enzymatic activity, i.e., enzymatic activity like Factor C from a horseshoe crab as described herein elsewhere.

In the present invention, "percentage (%) of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity", in the context of two or more nucleic acids or polypeptide sequences, refer to two or more sequences or sub-sequences that are the same or have a specified percentage of amino acid resides or nucleotides that are the same, when compared and aligned for maximum correspondence over a comparison window, or designated region as measured using one of the following sequence comparison algorithms or by manual alignment and visual inspection. Such sequences are then said to be "substantially identical". This definition also refers to the complement of a test sequence. Optionally, the identity exists over a region that is at least about 50 amino acids or nucleotides in length, or more preferably over a region that is 75-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

The terms nucleic acid molecule and nucleic acid sequence may be used herein interchangeably.

As discussed herein, there are numerous variants of the proteins and polypeptides of the present invention. Protein variants and derivatives are well understood to those of skill in the art and in can involve amino acid sequence modifications. For example, amino acid sequence modifications typically fall into one or more of three classes: substitutional, insertional or deletional variants. Insertions include amino and/or carboxyl terminal fusions as well as intrasequence insertions of single or multiple amino acid residues. Deletions are characterized by the removal of one or more amino acid residues from the protein sequence. Typically, no more than about from 2 to 6 residues are deleted at any one site within protein molecules according to the present invention. These variants ordinarily are prepared by site specific mutagenesis of nucleotides in the DNA of the polynucleotide encoding the protein, thereby producing DNA encoding the variant, and thereafter expressing the DNA in recombinant cell culture according to the present invention.

Techniques for making substitution mutations at predetermined sites in DNA having a known sequence are well known to the ones skilled in the art. Amino acid substitutions are typically of single residues, but can occur at a number of different locations at once; insertions usually will be on the order of about from 1 to 10 amino acid residues; and deletions will range about from 1 to 30 residues. Deletions or insertions preferably are made in adjacent pairs, i.e., a deletion of 2 residues or insertion of 2 residues. Substitutions, deletions, insertions or any combination thereof may be combined to arrive at a final construct. The mutations must not place the sequence out of reading frame and preferably will not create complementary regions that could produce secondary mRNA structure. Substitutional variants are those in which at least one amino acid residue has been removed and a different amino acid residue inserted in its place such that a conservative substitution is obtained. The meaning of a conservative substitution is well known to the person skilled in the art.

Certain post-translational modifications are the result of the action of the recombinant host cells of the present invention on the expressed polypeptide. Glutaminyl and asparaginyl residues are frequently post-translationally deamidated to the corresponding glutamyl and asparyl residues. Alternatively, these residues are deamidated under mildly acidic conditions. Other post-translational modifications include hydroxylation of proline and lysine, phosphorylation of hydroxyl groups of seryl or threonyl residues, methylation of the o-amino groups of lysine, arginine, and histidine side chains, acetylation of the N-terminal amine and, in some instances, amidation of the C-terminal carboxyl. Such post-translational modifications are also contemplated by the present invention.

The terms "protein" and "polypeptide" are used in the present invention interchangeably.

The terms "Factor C protein(s)" and "Factor C polypeptide(s)" may accordingly be used herein interchangeably.

When particular embodiments of the invention are described herein, the corresponding paragraphs/text passages of the description invariably make reference to means and/or methods described elsewhere in the description. In this context, terms like "according to the present invention", "of the present invention" and "provided by the present invention" are used. This means that when a particular embodiment of the invention is described in a certain paragraph or text passage, reference is made to means and/or methods "according to the present invention" or "of the present invention", which are described elsewhere in the present description. For a particular embodiment described, such references are intended to incorporate for the particular embodiment all means and/or methods, which are described elsewhere in the present description, and which are provided by the present invention and therefore form part of the scope of the invention. For example, if the description of a particular embodiment refers to "Factor C according to the present invention" or "Factor C of the present invention", or "Factor C produced by or obtained from a method of the present invention", it is intended that all Factor C proteins, which are described elsewhere in the description, and which are provided by the present invention and therefore form part of the scope of the invention, are applicable to that particular embodiment. This particularly applies, for example, to fragments and variants of Factor C proteins according to the present invention, which are defined in the present invention, and which are applicable to the various embodiments described throughout the application text.

The above principle applies to all embodiments making use of terms like "according to the present invention", "of the present invention" and/or "provided by the present invention". It goes without saying that not each embodiment described herein can specifically mention all the means and/or methods of the invention, which are already defined elsewhere in the description, and which are applicable to the various embodiments described throughout the application text. Otherwise, each patent application would comprise several hundreds of description pages.

Furthermore, terms like "in various embodiments" and "in various other/further embodiments" obviously mean "in various embodiments of the present invention" and "in various other/further embodiments of the present invention".

The invention is exemplified by the following examples, which are of illustrative nature only and should not be construed as limiting the scope of the present invention in any manner or to any extent.

EXAMPLES

Example 1: Cloning of Factor C Gene into Expression Vector and Transformation of *E. coli* DH5α

Starting point for cloning of Factor C gene into an expression vector was the Factor C sequence from *Tachypleus tridentatus* (NCBI Accession Number P28175.1; therein reference 1: Muta et al. 1991, J. Biol. Chem. 266 (10):6554-6561). The amino acid sequence of the wild type Factor C protein from *T. tridentatus* as shown under Accession Number P28175.1 has a length of 1,019 amino acid residues. The leader sequence, which is cleaved off after expression and secretion of the protein, has a length of 25 amino acid residues (residues 1-25 of the amino acid sequence shown under Accession Number P28175.1). The amino acid sequence of the wild type Factor C protein from *T. tridentatus* without the leader sequence is shown in SEQ ID NO: 2. The nucleotide sequence encoding wild type Factor C protein from *T. tridentatus* as shown in SEQ ID NO: 2 is given in SEQ ID NO: 1.

The *T. tridentatus* sequence of SEQ ID NO: 1 was codon-optimized for expression in *Leishmania*. The generated codon-optimized sequence is shown in SEQ ID NO: 3. The amino acid sequence encoded by the codon-optimized nucleotide sequence of SEQ ID NO: 3 is shown in SEQ ID NO: 4. The codon-optimization did not result in a change of the amino acid sequence of the amino acid sequence of the original wild type Factor C protein. Therefore, the amino acid sequence of SEQ ID NO: 4 is identical with the amino acid sequence of SEQ ID NO: 2.

The codon-optimized sequence of SEQ ID NO: 3 was cloned into an expression vector, and the resulting plasmid was subsequently transformed into *E. coli* DH5α.

Example 2: Transfection of *Leishmania* and Selection of Clones

Preparation of Expression Vectors for Transfection

A *Leishmania* host cell-specific expression vector was prepared, which comprises the codon-optimized sequence of SEQ ID NO: 3 and a signal peptide sequence for secretory expression of the target protein in *Leishmania* host cells. The amino acid sequence of the secretory signal peptide sequence from *Leishmania tarentolae* is shown in SEQ ID NO: 5. The *Leishmania* leader sequence is cleaved off after expression and secretion of the protein.

Transfection of *Leishmania* Cells

The stable DNA transfection of a wide range of trypanosomatids, including transfection of *Leishmania* by electroporation, has been described in the art (Beverly and Clayton 1993, Methods Mol. Biol. 21:333-348; Coburn et al. 1991, Mol. Biochem. Parasitol. 46: 169-179). Here, culturing and transfection of *Leishmania* cells was performed applying a High Voltage protocol for transfection (Jena Bioscience GmbH, Jena, Germany). In particular, *Leishmania* cells (*Leishmania tarentolae*) obtained from a preculture were cultured until a cell density of about $6\times10^7$ cells/ml was reached (OD 1.4). It was ensured by microscopy that the cells were vital and of drop-like shape. Pre-chilled cells were added to a tube with 0.1-5 μg transforming DNA (on ice), mixed and transferred to an electroporation cuvette (on ice). It was pulsed 2 times at 1,500 V, 25 µF with 10 sec. between pulses (pulse time ca. 0.3 msec.) using a genepulser with pulse controller. The cuvette was put back on ice for 10 minutes, and the electroporated cells were transferred into a ventilated tissue culture flask, followed by incubation over night at 26° C. as static suspension culture (about 20 hours, O.D. 0.3-0.4).

Selection of Clones

Selection of clones was done by plating on solid media supplemented with selective antibiotics. Single clones were then expanded in selective media. To this end, up to 10 clones were cultivated in 10 ml each in culture flasks. These cultures were used for evaluation.

Genomic DNA was isolated and the insertion of recombinant Factor C gene was confirmed by PCR using oligonucleotides specific for the recombinant Factor C gene.

The gene expression was analyzed by diluting the cultures 1:10 in fresh medium containing 10 µg/ml tetracycline for induction of expression. Cultures were grown at 26° C. in the dark for 3-4 days. Cells were harvested (3,000×g, 4° C., 10 minutes). Proteins in the supernatants were concentrated by trichloroactic acid (TCA) precipitation and analyzed by SDS-PAGE.

Example 3: Expression and Purification of Recombinant Factor C Protein

The recombinant protein expression in trypanosomatid protozoa, in particular in *Leishmania*, is described in the art (Breitling et al. 2002, Protein Expression and Purification 25:209-218; Basile and Peticca 2009, Mol. Biotechnol. 43:273-278). Here, culturing and engineering of *Leishmania* for expression and purification of Factor C protein was performed using a gene expression kit provided by Jena Bioscience GmbH, Jena, Germany.

3.1 Maintenance of Production Strains

Production strains were cultivated in 10 ml volume in culture flasks at 26° C. in the dark. Strains are serially diluted 1:20 or 1:50 every 2-3 days into fresh culture medium containing all additives and antibiotics for the selection of inserted genes.

After 3 month, cultured strains are discarded and a new culture was started from a fresh glycerol stock.

3.2 Expression

A pre-culture was set up by diluting the production strain 1:50 in fresh medium and incubating in culture flasks at 26° C. in the dark for 2-3 days.

1.5 l of culture medium containing tetracycline for induction of expression in an Erlenmeyer flask was inoculated with 30 ml of the pre-culture. Expression takes place at 23° C. in the dark and shaking at 105 rpm for 68-72 hours. When the concentration of glucose in the medium decreased below 650 mg/L, Hemin and Glucose were added and the culture was incubated for additional 86-72 hours.

Cells were harvested (4000×g, 4° C., 30 minutes). The supernatant was either frozen at −20° C. or directly used for purification of recombinant Factor C.

3.3 Purification 3.3.1 Cation Exchange Chromatography

Supernatant from expression was either used directly or gently thawed. After adding 2 mM EDTA, the supernatant was diluted with 20 mM potassium acetate, 2 mM EDTA pH 5 until a pH of 5.0-5.5 and a conductivity of <5.5 mS/cm was reached.

Purification was performed using cation exchange chromatography. An SP650M column was used with 25 mM potassium acetate, 2 mM EDTA pH 5 as equilibration buffer, and 25 mM potassium acetate, 2 mM EDTA, 1 M potassium chloride pH 5 as elution buffer. After uploading of the supernatant, the column was washed first with equilibration buffer, then with 10% elution buffer. Elution takes place at 50% elution buffer.

3.3.2 Protein Analysis

Fractions containing protein were analyzed by gel filtration and SDS PAGE concerning concentration and purity.

For gel filtration, 50 µl of each fraction were loaded onto a TSK3000 PW column with 0.75 ml/min. Absorption was followed at 220 nm. rFC elutes in a peak maximum with a retention time of 7.4+/−0.4 minutes.

Only fractions fulfilling the following criteria were pooled:

1) The peak area of the peak with a retention time of 6.4+/−0.4 minutes must not exceed 10% of the rFC peak area.
2) The peak area of the peak with a retention time of 10.3+/−0.5 minutes must not exceed 350% of the rFC peak area.
3) The minimum between rFC peak and the peak with a retention time of 10.3+/−0.5 minutes has to lie between 9 and 10 minutes, und the absorption value of the minimum must not exceed 30% of the absorption value of maximum of the rFC peak.

The concentration of rFC in each fraction was determined by the peak area with the help of an rFC standard curve. The concentration of the final pool has to be at least 50 µg/ml rFC.

3.3.3 Dialysis 1 mM PMSF was added to the rFC pool and incubated for 4 hours at room temperature. Subsequently 0.1% Pluronic® F-127 was added and the solution was dialysed against 5 litres of 5 mM potassium acetate, 100 mM potassium chloride, 0.1% Pluronic® F-127, 0.05 mM EDTA pH 5 at 4° C. Dialysis was performed 3 times for 12 hours each.

After the third dialysis, rFC solution was centrifuged (4000×g, 4° C., 1 hour) and the supernatant was again dialysed against 5 litres of 5 mM potassium acetate, 100 mM potassium chloride, 0.1% Pluronic® F-127, 0.05 mM EDTA pH 5 at 4° C. for at least 12 hours.

3.3.4 Storage

Dialysed rFC solution was sterile filtered, and the concentration was determined by gel filtration and purity by SDS Gel. The solution was stored at 4° C.

Example 4: Determination of the Specific Activity of Factor C Protein Produced in *Leishmania*

The specific activity of Factor C was determined according to the assay described in Ding et al. 1993 (Biochimica et Biophysica Acta 1202:149-156). This document has been cited in U.S. Pat. No. 5,712,144 for the assay, which was used to determine the specific activity of Factor C protein isolated from the horseshoe crab *C. rotundicauda.*

In particular, first a dilution series was made diluting Factor C protein produced in *Leishmania* in reaction buffer plus LPS. The reaction buffer comprises 50 mM Tris, 100 mM NaCl, and 50 mM $MgCl_2$, and was prepared using endotoxin-free ultrapure water. LPS was added to the reaction buffer from an LPS stock solution (LPS in dissolved in endotoxin-free ultrapure water).

A microtiter plate was loaded with the dilutions made and incubated for 1 hour at 37° C. Subsequently, a substrate for Factor C protein was added to the wells followed by incubation of the microtiter plate for 15 minutes at 37° C.

The substrate used was Boc-Val-Pro-Arg-AMC, which is a fluorogenic substrate for Factor C protein. Boc-VPR-AMC was dissolved in endotoxin-free ultrapure water to prepare a substrate solution, which was used for preparing dilutions of the substrate solution, which were applied to the assay.

After stopping the reaction by the addition of glacial acetic acid the fluorescence (RFU) was measured. The measured rfu values after 15 minutes substrate turnover at 37° C. are summarized in the following Table 1.

TABLE 1

Measured rfu values after 15 minutes substrate turnover at 37° C.

| rFC concentration (μg/ml) | rFC dilution factor | rFC + LPS (rfu) |
| --- | --- | --- |
| 5.3 | 1 | 19999 |
| 2.65 | 0.5 | 17571 |
| 1.325 | 0.25 | 12446 |
| 0.6625 | 0.125 | 8174 |
| 0.33125 | 0.0625 | 4360 |
| 0.165625 | 0.03125 | 1903 |
| 0.0828125 | 0.015625 | 669 |
| 0.04140625 | 0.0078125 | 148 |

Table 1 shows the rfu values of the LPS-activated rFC samples with signals higher than background after subtraction of background rfu values.

FIG. 1 shows the plot of measured rfu values after 15 minutes substrate turnover at 37° C. in dependence of the rFC concentration. The specific fluorescence of the fluorophor (AMC) was determined as 6,667 rfu/nmol under the experimental conditions described. For calculation of the rFC specific activity, the rFC concentration of 0.331 μg/ml was used. This corresponds to 0.0662 μg of rFC per well in the microtiter plate. According to this, 4,360 rfu/(15 min× 0.0662 μg rFC) were measured. This corresponds to 290.67 rfu/(min×0.0662 μg rFC). This in turn corresponds to 4,390,735 rfu/(min×mg rFC). This further corresponds to 658 nmol/(min×mg rFC), which in turn corresponds to 0.658 μmol/(min×mg rFC).

According to Ding et al. (1993), one unit is defined as 1 μmol of AMC hydrolyzed per min at 37° C. According to this definition and the above calculation, the recombinant Factor C has a specific activity of 0.658 Units/mg protein under the assay conditions described. The same specific activity was also found when using chymotrypsin for activation of the Factor C protein (data not shown).

As becomes clear from the assay setup, the specific activity was determined using Factor C protein activated by LPS. Therefore, this experiment shows that Factor C produced in *Leishmania* can be activated by LPS, and that the activated Factor C protein is enzymatically active, i.e., exhibits hydrolytic activity.

Example 5: Determination of the Molecular Weight of Factor C Protein Under Non-Reducing and Reducing Conditions on SDS-PAGE The molecular weight of Factor C protein produced in *Leishmania* has been determined under non-reducing and reducing conditions (SDS-PAGE). 50 μl of both reduced and non-reduced rFC sample as well as 20 μl molecular weight standard were loaded onto a 10 track VarioGel (4-12%). After electrophoresis was carried out in a vertical gel electrophoresis chamber, the gel was stained with ready-to-use PageBlue™ Protein Staining Solution (Fermentas) according to the manufacturer's protocol.

Rf values were calculated by division of the migration distance (in cm) of the protein bands and the total migration distance from the gel front (in cm). Rf values of marker proteins were plotted against the molecular weight of the marker proteins. The resulting curve was fitted by a logarithmic fitting algorithm. The molecular weight of the purified Factor C protein under non-reducing and reducing conditions, respectively, was calculated based on the generated standard curve fitting equation. According to the equation, the following molecular weights were calculated for Factor C:

TABLE 2

Rf values of purified Factor C under non-reducing and reducing SDS PAGE running conditions

| | migration distance [cm] | Rf values | Calculated molecular weight [kDa] |
| --- | --- | --- | --- |
| rFC ox | 7.1 | 0.33 | 102 |
| rFC red 1 | 8.9 | 0.41 | 69 |
| rFC red 2 | 12.6 | 0.58 | 37 |

The two-chain form of Factor C protein has a molecular weight of 102 kDa as determined by SDS-PAGE under non-reducing conditions (rFC ox). Under reducing conditions, a molecular weight of 69 kDa has been determined for the H-chain (rFC red 1), and a molecular weight of 37 kDa for the L-chain (rFC red 2).

The molecular weight of the H-chain and the L-chain under reducing conditions (rFC red 1+rFC red 2) combines to 106 kDa (including glycosylation).

```
SEQUENCE LISTING
SEQ ID NO: 1: The nucleotide sequence of the gene encoding wild
type Factor C protein from Tachypleus tridentatus without leader
sequence, length: 2,982 nucleotides.
                       agagg agtagatctg ggcttgtgtg atgaaacgag gttcgagtgt aagtgtggag atccaggcta tgtgttcaac gtccctatga aacaatgcac gtacttctat cgatggaggc cttattgtaa accatgtgat gacctggagg ctaaggacat ttgtccaaag tacaaacgat gtcaagagtg taaggctggt cttgatagtt gtgttacttg tccacctaac aaatatggta cttggtgtag cggtgaatgt caatgtaaga atggaggtat ctgtgaccag aggacaggag cttgtacctg tcgtgacaga tatgaaggag cgcactgtga aattctcaaa ggttgtcctc ttcttccatc ggattctcaa gttcaggaag tcagaaaccc accagataat ccccaaacta ttgactacag ctgttcacca gggttcaagc ttaaaggcgt ggcacgaatt
```

-continued

```
agctgtctcc caaatggaca gtggagtagc tttccaccca aatgtattcg agaatgtgcc aaggtttcat ctccagaaca cgggaaagtg aatgctccta gtggcaatat gatagaaggg gctactttac ggttctcatg tgatagtccc tactacttga ttggtcaaga acattaacc tgccagggta atggtcagtg gagtggacaa ataccacaat gtaagaagtt ggtcttctgt cctgaccttg atcctgtaaa ccatgctgaa caccaggtta aaattggtgt ggaacaaaaa tatggtcagt ttcctcaagg cactgaagtg acctatacgt gttcgggtaa ctacttcttg atgggtttta acaccttaaa atgtaaccct gatgggtcct ggtcaggatc acagccatcc tgtgttaaag tggcagacag agaggtcgac tgtgacagta aagctgtaga cttcttggat gatgttggtg aacctgtcag gatccactgt cctgctggct gttctttgac agctggtact gtgtggggta cagccatata ccacgaactt cctcagtgt gtcgtgcagc catccatgct ggcaagcttc caaactctgg aggggcggtg catgtagtga acaatggccc ctactcggac tttctgggta gtgacctgaa tgggataaaa tcggaagagt tgaagtctct tgcccgcagt tttcgatttg attatgtcag ttcatccaca gcaggtagat caggatgtcc tgatggatgg tttgaggtag aagagaactg tgtgtacgtt acatcaaaac agagagcctg ggaaagagct caaggtgtgt gtaccaatat ggctgctcgt cttgctgtgc tagacaaaga tctaattccg agttccttga ctgagactct acgagggaaa gggttaacaa ccacatggat aggattgcac agactagatg ctgagaagcc ctttgtttgg gagctaatgg atcgtagtaa tgtggttctg aatgataacc taacattctg ggcctctggc gaacctggaa atgaaactaa ctgtgtatat ctggacatcc gagatcagct gcagcctgtg tggaaaacca agtcatgttt tcagccctca agctttgctt gcatgatgga tttgtcagac agaaataaag ccaaatgcga tgaccctgga ccactggaaa atggacacgc cacacttcat ggacaaagta ttgatgggtt ctatgctggt tcttctataa ggtacagctg tgaggttctc cactacctca gtggaactga gaccgtaact tgtacaacaa atggcacatg gagtgctcct aaacctcgat gtatcaaagt catcacctgc caaaaccctc ctgtaccatc atatggttct gtggaaatca acccccaag tcggacaaac tcgatcagtc gtgttgggtc accttcttg aggttgccac ggttacccct cccattagcc agagcagcca aacctcctcc aaaacctaga tcctcacaac cctctactgt ggacttggct tctaaagtta aactacctga aggtcattac cgggtagggt ctcgagccat ttacacgtgc gagtcgagat actacgaact acttggatct caaggcagaa gatgtgactc taatggaaac tggagtggtc ggcccgctag ctgtattcca gtttgtggac ggtcagactc tcctcgttct cctttcatct ggaatgggaa ttctacagaa ataggtcagt ggccgtggca ggcaggaatc tctcgatggc ttgcagacca caatatgtgg tttctccagt gtggaggatc cctattgaat gagaaatgga tcgtcactgc tgcccactgt gtcacctact ctgctactgc tgagataatt gatcccagtc agtttaaaat ctatctgggc aagtactacc gtgatgacag tagagacgat gactacgtac aagtaagaga ggctctcgag atccacgtaa atcctaacta cgaccccggc aatctcaact ttgacatagc cctaattcaa ctgaaaactc ctgttacttt gacaacacga gtccaaccaa tctgtctgcc tactgacatc acaacaagag aacacttgaa ggagggaaca ttagcagtgg tgacaggttg gggtttgaat gaaaacaaca catattcaga gatgattcaa caagctgtgc tacctgttgt tgcagcaagc acctgtgaag aggggtacaa ggaagcagac ttaccactga cagtaacaga gaacatgttc tgtgcaggtt acaagaaggg acgttatgat gcctgcagtg gggacagtgg aggaccatta gtgtttgctg atgattccg taccgaaagg
```

-continued cggtgggtct tggaagggat tgtcagctgg ggcagtccca gtggatgtgg caaggctaac cagtatgggg gcttcactaa agttaacgtt tttctatcat ggattaggca gttcatt SEQ ID NO: 2: The amino acid sequence of the wild type Factor C
protein from Tachypleus tridentatus without leader sequence,
length: 994 amino acid residues.
rgvdlglcdetrfeckcgdpgyvfnvpmkqctyfyrwrpyckpcddleakdicpkykrcqeckagldscvtc ppnkygtwcsgecqcknggicdqrtgactcrdryegahceilkgcpllpsdsqvqevrnppdnpqtidyscs pgfklkgvarisclpngqwssfppkcirecakvsspehgkvnapsgnmiegatlrfscdspyyligqetltc qgngqwsgqipqckklvfcpdldpvnhaehqvkigveqkygqfpqgtevtytcsgnyflmgfntlkcnpdgs wsgsqpscvkvadrevdcdskavdflddvgepvrihcpagcsltagtvwgtaiyhelssvcraaihagklpn sggavhvvnngpysdflgsdlngikseelkslarsfrfdyvssstagrsgcpdgwfeveencvyvtskqraw eraqgvctnmaarlavldkdlipssltetlrgkglttwiglhrldaekpfvwelmdrsnvvlndnltfwas gepgnetncvyldirdqlqpvwktkscfqpssfacmmdlsdrnkakcddpgplenghatlhgqsidgfyags siryscevlhylsgtetvtcttngtwsapkprcikvitcqnppvpsygsveikppsrtnsisrvgspflrlp rlplplaraakpppkprssqpstvdlaskvklpeghyrvgsraiytcesryyellgsqgrrcdsngnwsgrp ascipvcgrsdsprspfiwngnsteigqwpwqagisrwladhnmwflqcggsllnekwivtaahcvtysata eiidpsqfkiylgkyyrddsrdddyvqvrealeihvnpnydpgnlnfdialiqlktpvtlttrvqpiclptd ittrehlkegtlavvtgwglnenntysemiqqavlpvvaastceegykeadlpltvtenmfcagykkgryda csgdsggplvfaddsrterrwvlegivswgspsgcgkanqyggftkvnvflswirqfi SEQ ID NO: 3: The nucleotide sequence of Factor C from T. tridentatus
without leader sequence, codon-optimized for expression in Leishmania,
length: 2,982 nucleotides.
aggggtgtggacctgggcctgtgcgacgagacccgcttcgagtgcaagtgcggcgacccgggctacgtgttc aacgtgccgatgaagcagtgcacgtacttctaccgctggcgcccgtactgcaagccgtgcgacgacctggag gcgaaggacatctgcccgaagtacaagcgctgccaggagtgcaaggcgggcctggacagctgcgtgacgtgc ccgccgaacaagtacggcacgtggtgcagcggcgagtgccagtgcaagaacggtggcatctgcgatcagcgc acgggcgcgtgcacatgccgcgatcgctacgagggcgcgcactgcgagatcctgaagggctgcccgctgctg ccgagcgacagccaggtgcaggaggtgcgcaacccgccggacaacccgcagacgatcgactactcgtgcagc cccggcttcaagctcaagggcgtggcgcgcatcagctgcctcccgaacggtcagtggtcgagcttcccgccg aagtgcatccgcgagtgcgcgaaggtgagcagcccggagcacggcaaggtgaacgcgccgagcggcaacatg atcgagggcgcgacgctgcgcttcagctgcgacagcccgtactacctgatcggccaggagaccctgacctgc cagggcaacggccagtggagcggccagatcccgcagtgcaagaagctggtcttctgcccggacctggacccg gtgaaccacgcggagcaccaggtgaagatcggcgtggagcagaagtacggccagttcccgcagggcacggag gtgacgtacacgtgcagcggcaactacttcctgatgggcttcaacacgctgaagtgcaacccggacggtagc tggtcgggcagccagccgtcctgcgtgaaggtggcggaccgcgaggtggactgcgacagcaaggcggtggac ttcctggacgacgtgggcgagccggtgcgcatccactgcccggctggctgcagcctgacagcgggcacggtg tggggcacggcgatctaccacgagctgtcgagcgtgtgccgcgctgcgatccacgcgggcaagctgccgaac agcggcggtgcggtgcacgtggtgaacaacggcccgtacagcgacttcctgggcagcgacctgaacggcatc aagagcgaggagctgaagagcctggcccgcagcttccgcttcgactacgtgagcagcagcacggctggtcgc agcggctgcccggacggctggttcgaggtggaggagaactgcgtctacgtcacgagcaagcag

```
aagagctgcttccagccgagctccttcgcgtgcatgatggacctgagcgaccgcaacaaggcgaagtgcgac
gacccgggtccgctggagaacggccacgcgacgctgcacggccagagcatcgacggcttctacgcgggcagc
agcatccgctacagctgcgaggtgctgcactacctgagcggcacggagaccgtgacgtgcacgacgaacggc
acgtggtccgcgccgaagccgcgctgcatcaaggtgatcacgtgccagaacccgccggtgccgagctacggc
agcgtggagatcaagccgccgtcgcgcacgaactcgattagccgcgtgggctcgccgttcctgcgtctgcca
cgcctcccactgccgctggctcgtgcggccaagccgccaccgaagccacgcagcagccagccgagcacggtg
gacctggccagcaaggtgaagctgccggagggccactaccgcgtgggctcgcgcgcgatctacacgtgcgag
agccgctactacgagctgctgggcagccagggtcgtcgctgcgacagcaacggcaactggagcggtcgcccg
gctagctgcatcccggtgtgcggtcgcagcgactccccgcgctcgccgttcatctggaacggcaacagcacg
gagatcggtcagtggcctggcaggcgggcatcagccgctggctggccgaccacaacatgtggttcctccag
tgcggcggcagcctgctgaacgagaagtggattgtgacggcggctcactgcgtgacgtactcggcgacggcc
gagatcatcgacccgagccagttcaagatctacctgggcaagtactaccgcgacgacagccgcgacgacgac
tacgtgcaggtgcgcgaggcgctggagatccacgtgaacccgaactacgacccgggcaacctgaacttcgat
atcgcgctgatccagctcaagacgccggtgacgctgacgacgcgcgtgcagccgatctgcctgccgacggac
atcacgacgcgcgagcacctgaaggagggcacgctggccgtcgtgacgggctggggcctgaacgagaacaac
acgtacagcgagatgatccagcaggcggtgctgccggtggtggcggcgagcacgtgcgaggagggctacaag
gaggcggacctgccgctgacggtgacggagaacatgttctgcgcgggctacaagaagggccgctacgacgcc
tgcagcggtgacagcggcggtccgctggtgttcgcggacgacagccgcacggagcgccgctgggtgctggag
ggcatcgtgagctggggcagcccgagcggttgcggcaaggcgaaccagtacggcggcttcacgaaggtgaac
gtgttcctcagctggatccgccagtttatc
```

SEQ ID NO: 4: The amino acid sequence encoded by the codon-optimized nucleotide sequence of Factor C protein from *Tachypleus tridentatus* without leader sequence as shown in SEQ ID NO: 3, length: 994 amino acid residues.

RGVDLGLCDETRFECKCGDPGYVFNVPMKQCTYFYRW

RPYCKPCDDLEAKDICPKYKRCQECKAGLDSCVTCPPNKYGTWCSGECQCKNGGICDQRT

GACTCRDRYEGAHCEILKGCPLLPSDSQVQEVRNPPDNPQTIDYSCSPGFKLKGVARISc

LPNGQWSSFPPKCIRECAKVSSPEHGKVNAPSGNMIEGATLRFSCDSPYYLIGQETLTCQ

GNGQWSGQIPQCKKLVFCPDLDPVNHAEHQVKIGVEQKYGQFPQGTEVTYTCSGNYFLMG

FNTLKCNPDGSWSGSQPSCVKVADREVDCDSKAVDFLDDVGEPVRIHCPAGCSLTAGTVW

GTAIYHELSSVCRAAIHAGKLPNSGGAVHVVNNGPYSDFLGSDLNGIKSEELKSLARSFR

FDYVSSSTAGRSGCPDGWFEVEENCVYVTSKQRAWERAQGVCTNMAARLAVLDKDLIPSS

LTETLRGKGLTTTWIGLHRLDAEKPFVWELMDRSNVVLNDNLTFWASGEPGNETNCVYLD

IRDQLQPVWKTKSCFQPSSFACMMDLSDRNKAKCDDPGPLENGHATLHGQSIDGFYAGSS

IRYSCEVLHYLSGTETVTCTTNGTWSAPKPRCIKVITCQNPPVPSYGSVEIKPPSRTNSI

SRVGSPFLRLPRLPLPLARAAKPPPKPRSSQPSTVDLASKVKLPEGHYRVGSRAIYTCES

RYYELLGSQGRRCDSNGNWSGRPASCIPVCGRSDSPRSPFIWNGNSTEIGQWPWQAGISR

-continued

WLADHNMWFLQCGGSLLNEKWIVTAAHCVTYSATAEIIDPSQFKIYLGKYYRDDSRDDDY

VQVREALEIHVNPNYDPGNLNFDIALIQLKTPVTLTTRVQPICLPTDITTREHLKEGTLA

VVTGWGLNENNTYSEMIQQAVLPVVAASTCEEGYKEADLPLTVTENMFCAGYKKGRYDAC

SGDSGGPLVFADDSRTERRWVLEGIVSWGSPSGCGKANQYGGFTKVNVFLSWIRQFI

SEQ ID NO: 5: The amino acid sequence of the secretory signal peptide sequence from *Leishmania tarentolae*, length: 23 amino acid residues.
MASRLVRVLAAAMLVAAAVSVDA

+++

---

The invention claimed is:

1. A method for detecting endotoxin in a sample suspected of containing endotoxin, the method comprising
   a) obtaining a recombinant horseshoe crab Factor C prepared by culturing a parasitic protozoan comprising a polynucleotide encoding horseshoe crab Factor C protein, said protozoan expressing a two-chain zymogen form of horseshoe crab Factor C protein having a molecular weight of about 102 kDa as determined by SDS-PAGE under non-reducing conditions, said zymogen being rendered enzymatically active upon contacting lipopolysaccharide and recovering the recombinant Factor C; and
   b) contacting the sample to be assayed for the presence of endotoxin with the recombinant horseshoe crab Factor C by measuring serine protease activity of the recombinant Factor C.

2. The method of claim 1, wherein the parasitic protozoan is a member of the order Trypanosomatida.

3. The method of claim 2, wherein the parasitic protozoan is a member of the genus *Leishmania*.

4. The method of claim 3, wherein the parasitic protozoan is *Leishmania tarentolae*.

5. The method of claim 1, wherein said polynucleotide encodes Factor C protein from *Limulus polyphemus, Carcinoscorpius rotundicauda, Tachypleus tridentatus*, or *Tachypleus gigas*.

6. The method of claim 1, wherein enzymatic activity of the recombinant Factor C is measured through the use of a chromogenic or fluorogenic substrate followed by chromogenic or fluorogenic detection.

7. The method of claim 6, wherein the substrate is a chromogenic peptidyl-pNA substrate or fluorogenic peptidyl-AMC, peptidyl-AFC, or peptidyl-MCA substrates.

8. The method of claim 7, wherein the substrate is N-t-Boc-VPR-MCA, N-t-BocVPR-AMC, Mu-VPR-AFC or Boc-VPR-pNA.

9. The method of claim 1, wherein the expressed Factor C protein is accumulated in the cell culture medium.

10. The method of claim 1, wherein said polynucleotide encodes Factor C protein having the amino acid sequence of SEQ ID NO: 4.

* * * * *

SEQUENCE LISTING

<160> NUMBER OF SEQ ID NOS: 5

<210> SEQ ID NO 1
<211> LENGTH: 2982
<212> TYPE: DNA
<213> ORGANISM: Tachypleus tridentatus

<400> SEQUENCE: 1

```
agaggagtag atctgggctt gtgtgatgaa acgaggttcg agtgtaagtg tggagatcca      60
ggctatgtgt tcaacgtccc tatgaaacaa tgcacgtact tctatcgatg gaggccttat     120
tgtaaaccat gtgatgacct ggaggctaag gacatttgtc aaagtacaa acgatgtcaa      180
gagtgtaagg ctggtcttga tagttgtgtt acttgtccac taacaaata tggtacttgg      240
tgtagcggtg aatgtcaatg taagaatgga ggtatctgtg accagaggac aggagcttgt    300
acctgtcgtg acagatatga aggagcgcac tgtgaaattc tcaaaggttg tcctcttctt    360
ccatcggatt ctcaagttca ggaagtcaga aacccaccag ataatcccca aactattgac    420
tacagctgtt caccagggtt caagcttaaa ggcgtggcac gaattagctg tctcccaaat    480
ggacagtgga gtagctttcc acccaaatgt attcgagaat gtgccaaggt tcatctcca     540
gaacacggga agtgaatgc tcctagtggc aatatgatag aaggggctac tttacggttc     600
tcatgtgata gtccctacta cttgattggt caagaaacat taacctgcca gggtaatggt     660
cagtggagtg gacaaatacc acaatgtaag aagttggtct tctgtcctga ccttgatcct    720
gtaaaccatg ctgaacacca ggttaaaatt ggtgtggaac aaaaatatgg tcagtttcct    780
caaggcactg aagtgaccta cgtgttcg ggtaactact tcttgatggg ttttaacacc      840
ttaaaatgta accctgatgg gtcctggtca ggatcacagc catcctgtgt taaagtggca    900
gacagagagg tcgactgtga cagtaaagct gtagacttct ggatgatgt tggtgaacct    960
gtcaggatcc actgtcctgc tggctgttct tgacagctg gtactgtgtg gggtacagcc   1020
ataccacg aactttcctc agtgtgtcgt gcagccatcc atgctggcaa gcttccaaac   1080
tctggagggg cggtgcatgt agtgaacaat ggcccctact cggactttct gggtagtgac   1140
ctgaatggga taaaatcgga agagttgaag tctcttgccc gcagttttcg atttgattat   1200
gtcagttcat ccacagcagg tagatcagga tgtcctgatg gatggtttga ggtagaagag   1260
aactgtgtgt acgttacatc aaaacagaga gcctgggaaa gagctcaagg tgtgtgtacc   1320
aatatggctg ctcgtcttgc tgtgctagac aaagatctaa ttccgagttc cttgactgag   1380
actctacgag ggaaagggtt aacaaccaca tggataggat tgcacagact agatgctgag   1440
aagccctttg tttgggagct aatggatcgt agtaatgtgg ttctgaatga taacctaaca   1500
ttctgggcct ctggcgaacc tggaaatgaa actaactgtg tatatctgga catccgagat   1560
```

-continued

```
cagctgcagc ctgtgtggaa aaccaagtca tgttttcagc cctcaagctt tgcttgcatg    1620
atggatttgt cagacagaaa taaagccaaa tgcgatgacc ctggaccact ggaaaatgga    1680
cacgccacac ttcatggaca aagtattgat gggttctatg ctggttcttc tataaggtac    1740
agctgtgagg ttctccacta cctcagtgga actgagaccg taacttgtac aacaaatggc    1800
acatggagtg ctcctaaacc tcgatgtatc aaagtcatca cctgccaaaa ccctcctgta    1860
ccatcatatg gttctgtgga aatcaaaccc caagtcgga caaactcgat cagtcgtgtt    1920
gggtcacctt tcttgaggtt gccacggtta ccctcccat tagccagagc agccaaacct    1980
cctccaaaac ctagatcctc acaaccctct actgtggact tggcttctaa agttaaacta    2040
cctgaaggtc attaccgggt agggtctcga gccatttaca cgtgcgagtc gagatactac    2100
gaactacttg gatctcaagg cagaagatgt gactctaatg gaaactggag tggtcggccc    2160
gctagctgta ttccagtttg tggacggtca gactctcctc gttctccttt catctggaat    2220
gggaattcta cagaaatagg tcagtggccg tggcaggcag gaatctctcg atggcttgca    2280
gaccacaata tgtggtttct ccagtgtgga ggatccctat tgaatgagaa atggatcgtc    2340
actgctgccc actgtgtcac ctactctgct actgctgaga taattgatcc cagtcagttt    2400
aaaatctatc tgggcaagta ctaccgtgat gacagtagag acgatgacta cgtacaagta    2460
agagaggctc tcgagatcca cgtaaatcct aactacgacc ccggcaatct caactttgac    2520
atagccctaa ttcaactgaa aactcctgtt actttgacaa cacgagtcca accaatctgt    2580
ctgcctactg acatcacaac aagagaacac ttgaaggagg gaacattagc agtggtgaca    2640
ggttggggtt tgaatgaaaa caacacatat tcagagatga ttcaacaagc tgtgctacct    2700
gttgttgcag caagcacctg tgaagagggg tacaaggaag cagacttacc actgacagta    2760
acagagaaca tgttctgtgc aggttacaag aagggacgtt atgatgcctg cagtggggac    2820
agtggaggac cattagtgtt tgctgatgat tcccgtaccg aaaggcggtg ggtcttggaa    2880
gggattgtca gctggggcag tcccagtgga tgtggcaagg ctaaccagta tggggcttc    2940 actaaagtta acgttttcct atcatggatt aggcagttca tt                       2982
```

<210> SEQ ID NO 2
<211> LENGTH: 994
<212> TYPE: PRT
<213> ORGANISM: Tachypleus tridentatus

<400> SEQUENCE: 2

```
Arg Gly Val Asp Leu Gly Leu Cys Asp Glu Thr Arg Phe Glu Cys Lys
1               5                   10                  15

Cys Gly Asp Pro Gly Tyr Val Phe Asn Val Pro Met Lys Gln Cys Thr
            20                  25                  30

Tyr Phe Tyr Arg Trp Arg Pro Tyr Cys Lys Pro Cys Asp Asp Leu Glu
        35                  40                  45

Ala Lys Asp Ile Cys Pro Lys Tyr Lys Arg Cys Gln Glu Cys Lys Ala
    50                  55                  60

Gly Leu Asp Ser Cys Val Thr Cys Pro Pro Asn Lys Tyr Gly Thr Trp
65                  70                  75                  80

Cys Ser Gly Glu Cys Gln Cys Lys Asn Gly Gly Ile Cys Asp Gln Arg
                85                  90                  95

Thr Gly Ala Cys Thr Cys Arg Asp Arg Tyr Glu Gly Ala His Cys Glu
            100                 105                 110

Ile Leu Lys Gly Cys Pro Leu Leu Pro Ser Asp Ser Gln Val Gln Glu
        115                 120                 125
```

```
Val Arg Asn Pro Pro Asp Asn Pro Gln Thr Ile Asp Tyr Ser Cys Ser
        130                 135                 140
Pro Gly Phe Lys Leu Lys Gly Val Ala Arg Ile Ser Cys Leu Pro Asn
145                 150                 155                 160
Gly Gln Trp Ser Ser Phe Pro Pro Lys Cys Ile Arg Glu Cys Ala Lys
                165                 170                 175
Val Ser Ser Pro Glu His Gly Lys Val Asn Ala Pro Ser Gly Asn Met
            180                 185                 190
Ile Glu Gly Ala Thr Leu Arg Phe Ser Cys Asp Ser Pro Tyr Tyr Leu
        195                 200                 205
Ile Gly Gln Glu Thr Leu Thr Cys Gln Gly Asn Gly Gln Trp Ser Gly
        210                 215                 220
Gln Ile Pro Gln Cys Lys Lys Leu Val Phe Cys Pro Asp Leu Asp Pro
225                 230                 235                 240
Val Asn His Ala Glu His Gln Val Lys Ile Gly Val Glu Gln Lys Tyr
            245                 250                 255
Gly Gln Phe Pro Gln Gly Thr Glu Val Thr Tyr Thr Cys Ser Gly Asn
            260                 265                 270
Tyr Phe Leu Met Gly Phe Asn Thr Leu Lys Cys Asn Pro Asp Gly Ser
        275                 280                 285
Trp Ser Gly Ser Gln Pro Ser Cys Val Lys Val Ala Asp Arg Glu Val
290                 295                 300
Asp Cys Asp Ser Lys Ala Val Asp Phe Leu Asp Asp Val Gly Glu Pro
305                 310                 315                 320
Val Arg Ile His Cys Pro Ala Gly Cys Ser Leu Thr Ala Gly Thr Val
            325                 330                 335
Trp Gly Thr Ala Ile Tyr His Glu Leu Ser Ser Val Cys Arg Ala Ala
            340                 345                 350
Ile His Ala Gly Lys Leu Pro Asn Ser Gly Gly Ala Val His Val Val
        355                 360                 365
Asn Asn Gly Pro Tyr Ser Asp Phe Leu Gly Ser Asp Leu Asn Gly Ile
        370                 375                 380
Lys Ser Glu Glu Leu Lys Ser Leu Ala Arg Ser Phe Arg Phe Asp Tyr
385                 390                 395                 400
Val Ser Ser Ser Thr Ala Gly Arg Ser Gly Cys Pro Asp Gly Trp Phe
                405                 410                 415
Glu Val Glu Glu Asn Cys Val Tyr Val Thr Ser Lys Gln Arg Ala Trp
                420                 425                 430
Glu Arg Ala Gln Gly Val Cys Thr Asn Met Ala Ala Arg Leu Ala Val
            435                 440                 445
Leu Asp Lys Asp Leu Ile Pro Ser Ser Leu Thr Glu Thr Leu Arg Gly
450                 455                 460
Lys Gly Leu Thr Thr Thr Trp Ile Gly Leu His Arg Leu Asp Ala Glu
465                 470                 475                 480
Lys Pro Phe Val Trp Glu Leu Met Asp Arg Ser Asn Val Val Leu Asn
                485                 490                 495
Asp Asn Leu Thr Phe Trp Ala Ser Gly Glu Pro Gly Asn Glu Thr Asn
            500                 505                 510
Cys Val Tyr Leu Asp Ile Arg Asp Gln Leu Gln Pro Val Trp Lys Thr
        515                 520                 525
Lys Ser Cys Phe Gln Pro Ser Ser Phe Ala Cys Met Met Asp Leu Ser
530                 535                 540
```

Asp Arg Asn Lys Ala Lys Cys Asp Asp Pro Pro Leu Glu Asn Gly
545                 550                 555                 560

His Ala Thr Leu His Gly Gln Ser Ile Asp Gly Phe Tyr Ala Gly Ser
            565                 570                 575

Ser Ile Arg Tyr Ser Cys Glu Val Leu His Tyr Leu Ser Gly Thr Glu
            580                 585                 590

Thr Val Thr Cys Thr Thr Asn Gly Thr Trp Ser Ala Pro Lys Pro Arg
        595                 600                 605

Cys Ile Lys Val Ile Thr Cys Gln Asn Pro Pro Val Pro Ser Tyr Gly
    610                 615                 620

Ser Val Glu Ile Lys Pro Pro Ser Arg Thr Asn Ser Ile Ser Arg Val
625                 630                 635                 640

Gly Ser Pro Phe Leu Arg Leu Pro Arg Leu Pro Leu Pro Leu Ala Arg
                645                 650                 655

Ala Ala Lys Pro Pro Lys Pro Arg Ser Ser Gln Pro Ser Thr Val
                660                 665                 670

Asp Leu Ala Ser Lys Val Lys Leu Pro Glu Gly His Tyr Arg Val Gly
            675                 680                 685

Ser Arg Ala Ile Tyr Thr Cys Glu Ser Arg Tyr Tyr Glu Leu Leu Gly
        690                 695                 700

Ser Gln Gly Arg Arg Cys Asp Ser Asn Gly Asn Trp Ser Gly Arg Pro
705                 710                 715                 720

Ala Ser Cys Ile Pro Val Cys Gly Arg Ser Asp Ser Pro Arg Ser Pro
                725                 730                 735

Phe Ile Trp Asn Gly Asn Ser Thr Glu Ile Gly Gln Trp Pro Trp Gln
            740                 745                 750

Ala Gly Ile Ser Arg Trp Leu Ala Asp His Asn Met Trp Phe Leu Gln
        755                 760                 765

Cys Gly Gly Ser Leu Leu Asn Glu Lys Trp Ile Val Thr Ala Ala His
770                 775                 780

Cys Val Thr Tyr Ser Ala Thr Ala Glu Ile Ile Asp Pro Ser Gln Phe
785                 790                 795                 800

Lys Ile Tyr Leu Gly Lys Tyr Tyr Arg Asp Asp Ser Arg Asp Asp Asp
                805                 810                 815

Tyr Val Gln Val Arg Glu Ala Leu Glu Ile His Val Asn Pro Asn Tyr
            820                 825                 830

Asp Pro Gly Asn Leu Asn Phe Asp Ile Ala Leu Ile Gln Leu Lys Thr
        835                 840                 845

Pro Val Thr Leu Thr Thr Arg Val Gln Pro Ile Cys Leu Pro Thr Asp
850                 855                 860

Ile Thr Thr Arg Glu His Leu Lys Glu Gly Thr Leu Ala Val Val Thr
865                 870                 875                 880

Gly Trp Gly Leu Asn Glu Asn Asn Thr Tyr Ser Glu Met Ile Gln Gln
                885                 890                 895

Ala Val Leu Pro Val Val Ala Ala Ser Thr Cys Glu Glu Gly Tyr Lys
            900                 905                 910

Glu Ala Asp Leu Pro Leu Thr Val Thr Glu Asn Met Phe Cys Ala Gly
        915                 920                 925

Tyr Lys Lys Gly Arg Tyr Asp Ala Cys Ser Gly Asp Ser Gly Gly Pro
            930                 935                 940

Leu Val Phe Ala Asp Asp Ser Arg Thr Glu Arg Arg Trp Val Leu Glu
945                 950                 955                 960

Gly Ile Val Ser Trp Gly Ser Pro Ser Gly Cys Gly Lys Ala Asn Gln

```
                965                 970                 975
Tyr Gly Gly Phe Thr Lys Val Asn Val Phe Leu Ser Trp Ile Arg Gln
            980                 985                 990
Phe Ile
```

<210> SEQ ID NO 3
<211> LENGTH: 2982
<212> TYPE: DNA
<213> ORGANISM: Artificial Sequence
<220> FEATURE:
<223> OTHER INFORMATION: Nucleotide sequence of synthetic Factor C gene
      (nucleotide sequence of Factor C from Tachypleus tridentatus codon
      optimized for expression in Leishmania)

<400> SEQUENCE: 3

```
aggggtgtgg acctgggcct gtgcgacgag acccgcttcg agtgcaagtg cggcgacccg      60
ggctacgtgt tcaacgtgcc gatgaagcag tgcacgtact tctaccgctg cgcccgtac     120
tgcaagccgt cgacgacct ggaggcgaag acatctgcc cgaagtacaa cgctgccag      180
gagtgcaagg cgggcctgga cagctgcgtg acgtgcccgc gaacaagta cggcacgtgg     240
tgcagcggcg agtgccagtg caagaacggt ggcatctgcg atcagcgcac gggcgcgtgc   300
acatgccgcg atcgctacga gggcgcgcac tgcgagatcc tgaagggctg cccgctgctg   360
ccgagcgaca gccaggtgca ggaggtgcgc aacccgccgg acaacccgca gacgatcgac   420
tactcgtgca gccccggctt caagctcaag ggcgtggcgc gcatcagctg cctcccgaac   480
ggtcagtggt cgagcttccc gccgaagtgc atccgcgagt gcgcgaaggt gagcagcccg   540
gagcacggca aggtgaacgc gccgagcggc aacatgatcg agggcgcgac gctgcgcttc   600
agctgcgaca gcccgtacta cctgatcggc caggagaccc tgacctgcca gggcaacggc   660
cagtggagcg gccagatccc gcagtgcaag aagctggtct ctgcccggg cctggacccg    720
gtgaaccacg cggagcacca ggtgaagatc ggcgtggagc agaagtacgg ccagttcccg   780
cagggcacgg aggtgacgta cacgtgcagc ggcaactact tcctgatggg cttcaacacg   840
ctgaagtgca acccggacgg tagctggtcg ggcagccagc cgtcctgcgt gaaggtggcg   900
gaccgcgagg tggactgcga cagcaaggcg gtggacttcc tggacgacgt gggcgagccg   960
gtgcgcatcc actgcccggc tggctgcagc ctgacagcgg gcacggtgtg gggcacggcg  1020
atctaccacg agctgtcgag cgtgtgccgc gctgcgatcc acgcgggcaa gctgccgaac  1080
agcggcggtg cggtgcacgt ggtgaacaac ggcccgtaca gcgacttcct gggcagcgac  1140
ctgaacggca tcaagagcga ggagctgaag agcctggccc gcagcttccg cttcgactac  1200
gtgagcagca gcacggctgg tcgcagcggc tgcccggacg gctggttcga ggtggaggag  1260
aactgcgtct acgtcacgag caagcagcgc gtgtgggagc gcgcgcaggg cgtgtgcacg  1320
aacatggcgg ctcgcctggc cgtgctggac aaggacctga tccgagcag cctgacggag  1380
accctgcgcg gcaagggcct gacgacgacg tggatcggcc tgcaccgcct ggacgcggag  1440
aagccgttcg tgtgggagct gatggaccgc agcaacgtgg tgctgaacga caacctgacg  1500
ttctgggcga gcgcgagcc gggcaacgag accaactgcg tgtacctgga catccgcgac  1560
cagctgcagc cggtgtggaa gacgaagagc tgcttccagc cgagctcctt cgcgtgcatg  1620
atggacctga gcgaccgcaa caaggcgaag tgcgacgacc cgggtccgct ggagaacggc  1680
cacgcgacgc tgcacggcca gagcatcgac ggcttctacg cgggcagcag catccgctac  1740
agctgcgagg tgctgcacta cctgagcggc acggagaccg tgacgtgcac gacgaacggc  1800
```

```
acgtggtccg cgccgaagcc gcgctgcatc aaggtgatca cgtgccagaa cccgccggtg    1860
ccgagctacg gcagcgtgga gatcaagccg ccgtcgcgca cgaactcgat tagccgcgtg    1920
ggctcgccgt tcctgcgtct gccacgcctc ccactgccgc tggctcgtgc ggccaagccg    1980
ccaccgaagc cacgcagcag ccagccgagc acggtggacc tggccagcaa ggtgaagctg    2040
ccggagggcc actaccgcgt gggctcgcgc gcgatctaca cgtgcgagag ccgctactac    2100
gagctgctgg cagccaggg tcgtcgctgc gacagcaacg gcaactggag cggtcgcccg    2160
gctagctgca tcccggtgtg cggtcgcagc gactccccgc gctcgccgtt catctggaac    2220
ggcaacagca cggagatcgg tcagtggccc tggcaggcgg gcatcagccg ctggctggcc    2280
gaccacaaca tgtggttcct ccagtgcggc ggcagcctgc tgaacgagaa gtggattgtg    2340
acggcggctc actgcgtgac gtactcggcg acggccgaga tcatcgaccc gagccagttc    2400
aagatctacc tgggcaagta ctaccgcgac gacagccgcg acgacgacta cgtgcaggtg    2460
cgcgaggcgc tggagatcca cgtgaacccg aactacgacc cggcaacct gaacttcgat    2520 atcgcgctga tccagctcaa gacgccggtg acgctgacga cgcgcgtgca gccgatctgc    2580
ctgccgacgg acatcacgac gcgcgagcac ctgaaggagg gcacgctggc cgtcgtgacg    2640
ggctggggcc tgaacgagaa caacacgtac agcgagatga tccagcaggc ggtgctgccg    2700
gtggtggcgg cgagcacgtg cgaggagggc tacaaggagg cggacctgcc gctgacggtg    2760
acggagaaca tgttctgcgc gggctacaag aagggccgct acgacgcctg cagcggtgac    2820
agcggcggtc cgctggtgtt cgcggacgac agccgcacgg agcgccgctg ggtgctggag    2880
ggcatcgtga gctggggcag cccgagcggt tgcggcaagg cgaaccagta cggcggcttc    2940
acgaaggtga acgtgttcct cagctggatc cgccagttta tc                      2982
```

<210> SEQ ID NO 4
<211> LENGTH: 994
<212> TYPE: PRT
<213> ORGANISM: Artificial Sequence
<220> FEATURE:
<223> OTHER INFORMATION: Amino acid sequence of synthetic Factor C protein (amino acid sequence encoded by the codon optimized nucleotide sequence of SEQ ID NO: 3)

<400> SEQUENCE: 4

```
Arg Gly Val Asp Leu Gly Leu Cys Asp Glu Thr Arg Phe Glu Cys Lys
1               5                   10                  15

Cys Gly Asp Pro Gly Tyr Val Phe Asn Val Pro Met Lys Gln Cys Thr
            20                  25                  30

Tyr Phe Tyr Arg Trp Arg Pro Tyr Cys Lys Pro Cys Asp Asp Leu Glu
        35                  40                  45

Ala Lys Asp Ile Cys Pro Lys Tyr Lys Arg Cys Gln Glu Cys Lys Ala
    50                  55                  60

Gly Leu Asp Ser Cys Val Thr Cys Pro Pro Asn Lys Tyr Gly Thr Trp
65                  70                  75                  80

Cys Ser Gly Glu Cys Gln Cys Lys Asn Gly Gly Ile Cys Asp Gln Arg
                85                  90                  95

Thr Gly Ala Cys Thr Cys Arg Asp Arg Tyr Glu Gly Ala His Cys Glu
            100                 105                 110

Ile Leu Lys Gly Cys Pro Leu Leu Pro Ser Asp Ser Gln Val Gln Glu
        115                 120                 125

Val Arg Asn Pro Pro Asp Asn Pro Gln Thr Ile Asp Tyr Ser Cys Ser
    130                 135                 140
```

```
Pro Gly Phe Lys Leu Lys Gly Val Ala Arg Ile Ser Cys Leu Pro Asn
145                 150                 155                 160

Gly Gln Trp Ser Ser Phe Pro Pro Lys Cys Ile Arg Glu Cys Ala Lys
                165                 170                 175

Val Ser Ser Pro Glu His Gly Lys Val Asn Ala Pro Ser Gly Asn Met
            180                 185                 190

Ile Glu Gly Ala Thr Leu Arg Phe Ser Cys Asp Ser Pro Tyr Tyr Leu
        195                 200                 205

Ile Gly Gln Glu Thr Leu Thr Cys Gln Gly Asn Gly Gln Trp Ser Gly
    210                 215                 220

Gln Ile Pro Gln Cys Lys Lys Leu Val Phe Cys Pro Asp Leu Asp Pro
225                 230                 235                 240

Val Asn His Ala Glu His Gln Val Lys Ile Gly Val Glu Gln Lys Tyr
                245                 250                 255

Gly Gln Phe Pro Gln Gly Thr Glu Val Thr Tyr Thr Cys Ser Gly Asn
                260                 265                 270

Tyr Phe Leu Met Gly Phe Asn Thr Leu Lys Cys Asn Pro Asp Gly Ser
            275                 280                 285

Trp Ser Gly Ser Gln Pro Ser Cys Val Lys Val Ala Asp Arg Glu Val
    290                 295                 300

Asp Cys Asp Ser Lys Ala Val Asp Phe Leu Asp Asp Val Gly Glu Pro
305                 310                 315                 320

Val Arg Ile His Cys Pro Ala Gly Cys Ser Leu Thr Ala Gly Thr Val
                325                 330                 335

Trp Gly Thr Ala Ile Tyr His Glu Leu Ser Ser Val Cys Arg Ala Ala
            340                 345                 350

Ile His Ala Gly Lys Leu Pro Asn Ser Gly Gly Ala Val His Val Val
        355                 360                 365

Asn Asn Gly Pro Tyr Ser Asp Phe Leu Gly Ser Asp Leu Asn Gly Ile
    370                 375                 380

Lys Ser Glu Glu Leu Lys Ser Leu Ala Arg Ser Phe Arg Phe Asp Tyr
385                 390                 395                 400

Val Ser Ser Ser Thr Ala Gly Arg Ser Gly Cys Pro Asp Gly Trp Phe
                405                 410                 415

Glu Val Glu Glu Asn Cys Val Tyr Val Thr Ser Lys Gln Arg Ala Trp
                420                 425                 430

Glu Arg Ala Gln Gly Val Cys Thr Asn Met Ala Ala Arg Leu Ala Val
            435                 440                 445

Leu Asp Lys Asp Leu Ile Pro Ser Ser Leu Thr Glu Thr Leu Arg Gly
        450                 455                 460

Lys Gly Leu Thr Thr Thr Trp Ile Gly Leu His Arg Leu Asp Ala Glu
465                 470                 475                 480

Lys Pro Phe Val Trp Glu Leu Met Asp Arg Ser Asn Val Val Leu Asn
                485                 490                 495

Asp Asn Leu Thr Phe Trp Ala Ser Gly Glu Pro Gly Asn Glu Thr Asn
            500                 505                 510

Cys Val Tyr Leu Asp Ile Arg Asp Gln Leu Gln Pro Val Trp Lys Thr
        515                 520                 525

Lys Ser Cys Phe Gln Pro Ser Ser Phe Ala Cys Met Met Asp Leu Ser
    530                 535                 540

Asp Arg Asn Lys Ala Lys Cys Asp Asp Pro Gly Pro Leu Glu Asn Gly
545                 550                 555                 560

His Ala Thr Leu His Gly Gln Ser Ile Asp Gly Phe Tyr Ala Gly Ser
```

```
                        565                 570                 575
Ser Ile Arg Tyr Ser Cys Glu Val Leu His Tyr Leu Ser Gly Thr Glu
                    580                 585                 590

Thr Val Thr Cys Thr Thr Asn Gly Thr Trp Ser Ala Pro Lys Pro Arg
                595                 600                 605

Cys Ile Lys Val Ile Thr Cys Gln Asn Pro Pro Val Pro Ser Tyr Gly
            610                 615                 620

Ser Val Glu Ile Lys Pro Pro Ser Arg Thr Asn Ser Ile Ser Arg Val
625                 630                 635                 640

Gly Ser Pro Phe Leu Arg Leu Pro Arg Leu Pro Leu Pro Leu Ala Arg
                645                 650                 655

Ala Ala Lys Pro Pro Lys Pro Arg Ser Ser Gln Pro Ser Thr Val
                660                 665                 670

Asp Leu Ala Ser Lys Val Lys Leu Pro Glu Gly His Tyr Arg Val Gly
            675                 680                 685

Ser Arg Ala Ile Tyr Thr Cys Glu Ser Arg Tyr Tyr Glu Leu Leu Gly
        690                 695                 700

Ser Gln Gly Arg Arg Cys Asp Ser Asn Gly Asn Trp Ser Gly Arg Pro
705                 710                 715                 720

Ala Ser Cys Ile Pro Val Cys Gly Arg Ser Asp Ser Pro Arg Ser Pro
                725                 730                 735

Phe Ile Trp Asn Gly Asn Ser Thr Glu Ile Gly Gln Trp Pro Trp Gln
                740                 745                 750

Ala Gly Ile Ser Arg Trp Leu Ala Asp His Asn Met Trp Phe Leu Gln
            755                 760                 765

Cys Gly Gly Ser Leu Leu Asn Glu Lys Trp Ile Val Thr Ala Ala His
770                 775                 780

Cys Val Thr Tyr Ser Ala Thr Ala Glu Ile Ile Asp Pro Ser Gln Phe
785                 790                 795                 800

Lys Ile Tyr Leu Gly Lys Tyr Tyr Arg Asp Asp Ser Arg Asp Asp Asp
                805                 810                 815

Tyr Val Gln Val Arg Glu Ala Leu Glu Ile His Val Asn Pro Asn Tyr
                820                 825                 830

Asp Pro Gly Asn Leu Asn Phe Asp Ile Ala Leu Ile Gln Leu Lys Thr
            835                 840                 845

Pro Val Thr Leu Thr Thr Arg Val Gln Pro Ile Cys Leu Pro Thr Asp
        850                 855                 860

Ile Thr Thr Arg Glu His Leu Lys Glu Gly Thr Leu Ala Val Val Thr
865                 870                 875                 880

Gly Trp Gly Leu Asn Glu Asn Asn Thr Tyr Ser Glu Met Ile Gln Gln
                885                 890                 895

Ala Val Leu Pro Val Val Ala Ala Ser Thr Cys Glu Glu Gly Tyr Lys
                900                 905                 910

Glu Ala Asp Leu Pro Leu Thr Val Thr Glu Asn Met Phe Cys Ala Gly
            915                 920                 925

Tyr Lys Lys Gly Arg Tyr Asp Ala Cys Ser Gly Asp Ser Gly Gly Pro
        930                 935                 940

Leu Val Phe Ala Asp Asp Ser Arg Thr Glu Arg Arg Trp Val Leu Glu
945                 950                 955                 960

Gly Ile Val Ser Trp Gly Ser Pro Ser Gly Cys Gly Lys Ala Asn Gln
                965                 970                 975

Tyr Gly Gly Phe Thr Lys Val Asn Val Phe Leu Ser Trp Ile Arg Gln
                980                 985                 990
```

-continued

```
Phe Ile

<210> SEQ ID NO 5
<211> LENGTH: 23
<212> TYPE: PRT
<213> ORGANISM: Leishmania tarentolae

<400> SEQUENCE: 5

Met Ala Ser Arg Leu Val Arg Val Leu Ala Ala Met Leu Val Ala
1               5                   10                  15

Ala Ala Val Ser Val Asp Ala
            20
```